US011756650B2

(12) United States Patent
Plotkin

(10) Patent No.: US 11,756,650 B2
(45) Date of Patent: Sep. 12, 2023

(54) SYSTEMS AND METHODS FOR PREDICTING MISFOLDED PROTEIN EPITOPES BY COLLECTIVE COORDINATE BIASING

(71) Applicant: The University of British Columbia, Vancouver (CA)

(72) Inventor: Steven Samuel Plotkin, Vancouver (CA)

(73) Assignee: The University of British Columbia, Vancouver (CA)

(*) Notice: Subject to any disclaimer, the term of this patent is extended or adjusted under 35 U.S.C. 154(b) by 1063 days.

(21) Appl. No.: 15/774,909

(22) PCT Filed: Nov. 9, 2016

(86) PCT No.: PCT/CA2016/051306
§ 371 (c)(1),
(2) Date: May 9, 2018

(87) PCT Pub. No.: WO2017/079836
PCT Pub. Date: May 18, 2017

(65) Prior Publication Data
US 2018/0330045 A1 Nov. 15, 2018

Related U.S. Application Data

(60) Provisional application No. 62/393,615, filed on Sep. 12, 2016, provisional application No. 62/365,634, filed on Jul. 22, 2016, provisional application No. 62/363,566, filed on Jul. 18, 2016, provisional application No. 62/352,346, filed on Jun. 20, 2016, provisional application No. 62/331,925, filed on May 4, 2016, provisional application No. 62/309,765, filed on Mar. 17, 2016, provisional application No. 62/289,893, filed on Feb. 1, 2016, provisional application No. 62/253,044, filed on Nov. 9, 2015.

(51) Int. Cl.
*G01N 33/48* (2006.01)
*G16B 15/20* (2019.01)
*G16B 15/00* (2019.01)

(52) U.S. Cl.
CPC ............. *G16B 15/20* (2019.02); *G16B 15/00* (2019.02)

(58) Field of Classification Search
None
See application file for complete search history.

(56) References Cited

U.S. PATENT DOCUMENTS

| | | | |
|---|---|---|---|
| 9,216,217 B2 | 12/2015 | Cashman | |
| 2001/0000807 A1 | 5/2001 | Freire | |
| 2010/0233176 A1 | 9/2010 | Cashman et al. | |
| 2011/0172981 A1 | 7/2011 | Al-Hashimi et al. | |

FOREIGN PATENT DOCUMENTS

| | | |
|---|---|---|
| CN | 103827875 A | 5/2014 |
| JP | 2012504801 A | 2/2012 |
| JP | 2013084255 A | 5/2013 |
| WO | 2017/079831 A1 | 5/2017 |
| WO | 2017/079832 A1 | 5/2017 |
| WO | 2017/079833 A1 | 5/2017 |
| WO | 2017/079834 A1 | 5/2017 |
| WO | 2017/079835 A1 | 5/2017 |

OTHER PUBLICATIONS

Li, Pai-Chi. Molecular dynamics simulations of the mechanical unfolding of proteins. Diss. 2006.*
Brooks, Bernard R., et al. "CHARMM: a program for macromolecular energy, minimization, and dynamics calculations." Journal of computational chemistry 4.2 (1983): 187-217.*
Allen, Michael P., and Dominic J. Tildesley. Computer simulation of liquids. Oxford university press, 1987.*
Piana, Stefano, and Alessandro Laio. "A bias-exchange approach to protein folding." The journal of physical chemistry B 111.17 (2007): 4553-4559.*
Markwick, Phineus RL, and J. Andrew McCammon. "Studying functional dynamics in bio-molecules using accelerated molecular dynamics." Physical Chemistry Chemical Physics 13.45 (2011): 20053-20065.*
Fiorin, Giacomo, Michael L. Klein, and Jérôme Hénin. "Using collective variables to drive molecular dynamics simulations." Molecular Physics 111.22-23 (2013): 3345-3362.*
Ausaf Ali, Syed, et al. "A review of methods available to estimate solvent-accessible surface areas of soluble proteins in the folded and unfolded states." Current Protein and Peptide Science 15.5 (2014): 456-476.*
Paci, Emanuele, and Martin Karplus. "Forced unfolding of fibronectin type 3 modules: an analysis by biased molecular dynamics simulations." Journal of molecular biology 288.3 (1999): 441-459.*
Bonomi, Massimiliano et al. PLUMED: a portable plugin for free-energy calculations with molecular dynamics. Computer Physics Communications 180(2009) 1961-1972.

(Continued)

*Primary Examiner* — Anna Skibinsky
(74) *Attorney, Agent, or Firm* — Bereskin & Parr LLP; Carmela De Luca

(57) ABSTRACT

Methods predict candidate epitopes in a protein by: providing a conformational sampling engine; obtaining a model of a protein suitable for use with the conformational sampling engine and comprising a native structure; applying a collective coordinate bias to the protein model, the collective coordinate bias causing the conformational sampling engine to in turn force the protein model to at least partially unfold from its native structure to an updated structure, wherein the collective coordinate bias is applied globally to at least a substantial portion of the protein model and is impartial as to where, within the substantial portion of the protein model, unfolding occurs; and analyzing the updated structure to identify one or more candidate epitopes, where the one or more candidate epitopes exhibit indicia of localized unfolding.

18 Claims, 16 Drawing Sheets

Specification includes a Sequence Listing.

(56) References Cited

OTHER PUBLICATIONS

Camacho, Carlos J. et al. Kinetics and thermodynamics of folding in model proteins. Proc. Natl. Acad. Sci. USA, 90(13):6369-6372, Jul. 1, 1993.

Das, A. et al. Unfolded protein ensembles, folding trajectories, and refolding rate prediction. The Journal of Chemical Physics. 139(12): 121925, 2013.

Vanommeslaeghe, K. et al. CHARMM General Force Field (CGenFF): A force field for drug-like molecules compatible with the CHARMM all-atom additive biological force fields. J Comput Chem. Mar. 2010. 31(4):671-690.

Bjelkmar, P. et al. Implementation of the CHARMM force field in GROMACS: analysis of protein stability effects from correlation maps, virtual interaction sites, and water models. J. Chem. Theo. Comp., 6:459-466, 2010.

Bard, Frederique et al. Epitope and isotype specificities of antibodies to β-amyloid peptide for protection against Alzheimer's disease-like neuropathology. Proc. Natl. Acad. Sci. USA, 100(4):2023-2028, 2003.

Kannan S. et al. Enhanced sampling of peptide and protein conformations using replica exchange simulations with a peptide backbone biasing-potential. Proteins: structure, function, and bioinformatics. Feb. 15, 2007. 66(3): 697-706.

Lapelosa M. et al. In Silico Vaccine Design Based on Molecular Simulations of Rhinovirus Chimeras Presenting HIV-1 gp41 Epitopes. Journal of molecular biology, Academic Press, United Kingdom. Jan. 16, 2009. 385(2): 675-691.

Zhuravlev P.I. et al. Propensity to Form Amyloid Fibrils Is Encoded as Excitations in the Free Energy Landscape of Monomeric Proteins. Journal of molecular biology, Academic Press, United Kingdom. May 17, 2014. 426(14): 2653-2666.

Das A., et al. Mechanical Probes of SOD1 Predict Systematic Trends in Metal and Dimer Affinity of ALS-Associated Mutants. Journal of molecular biology. Academic Press, United Kingdom. Jan. 3, 2013. 425(5): 850-874.

* cited by examiner

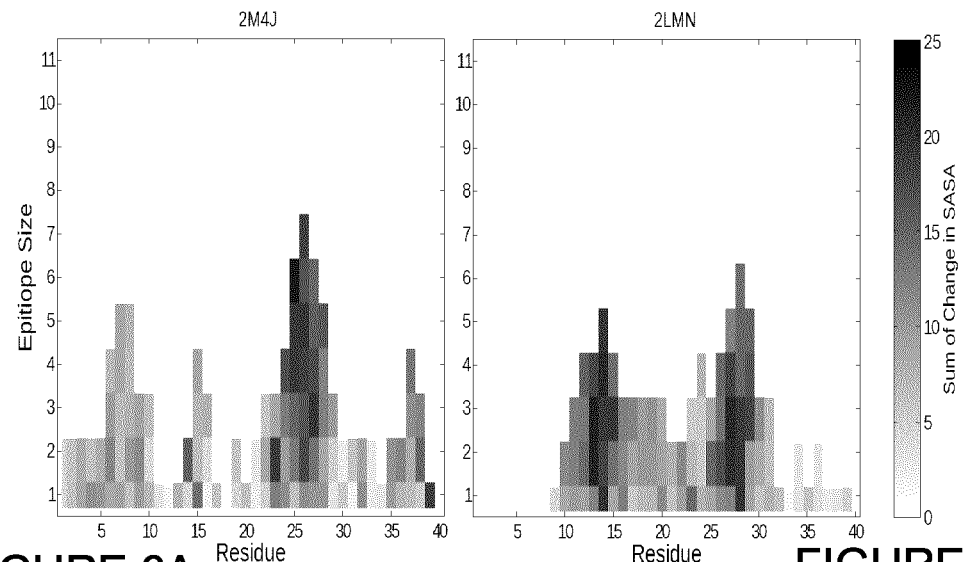
FIGURE 6A
FIGURE 6B
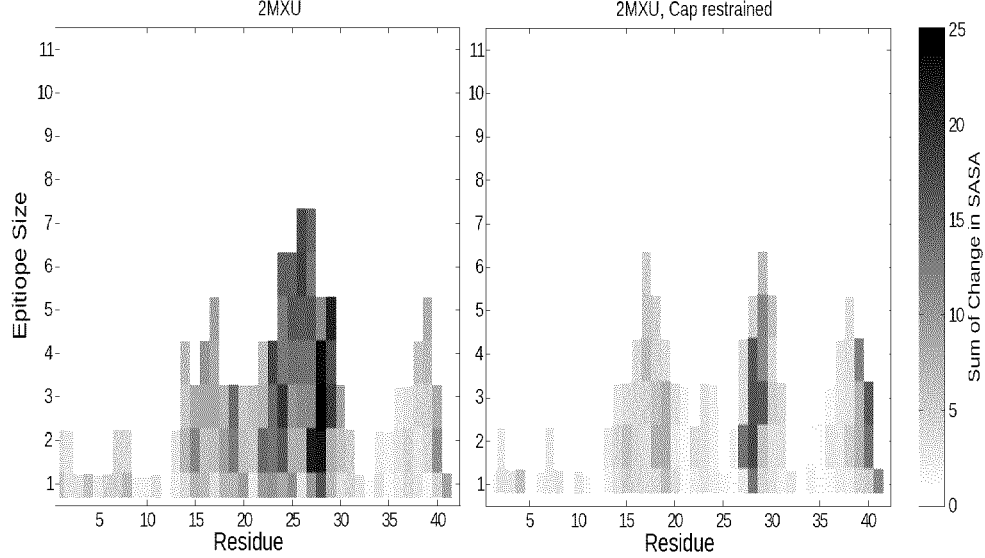
FIGURE 6C
FIGURE 6D

SEQUENCE LISTING

```
<160> NUMBER OF SEQ ID NOS: 42

<210> SEQ ID NO 1
<211> LENGTH: 6
<212> TYPE: PRT
<213> ORGANISM: Homo Sapiens

<400> SEQUENCE: 1

His His Gln Lys Leu Val
1               5

<210> SEQ ID NO 2
<211> LENGTH: 4
<212> TYPE: PRT
<213> ORGANISM: Homo Sapiens

<400> SEQUENCE: 2

His Asp Ser Gly
1

<210> SEQ ID NO 3
<211> LENGTH: 4
<212> TYPE: PRT
<213> ORGANISM: Homo Sapiens

<400> SEQUENCE: 3

His His Gln Lys
1

<210> SEQ ID NO 4
<211> LENGTH: 4
<212> TYPE: PRT
<213> ORGANISM: Homo Sapiens

<400> SEQUENCE: 4

Gln Lys Leu Val
1

<210> SEQ ID NO 5
<211> LENGTH: 4
<212> TYPE: PRT
<213> ORGANISM: Homo Sapiens

<400> SEQUENCE: 5

Ala Glu Asp Val
1

<210> SEQ ID NO 6
<211> LENGTH: 4
<212> TYPE: PRT
<213> ORGANISM: Homo Sapiens

<400> SEQUENCE: 6

Gly Gly Val Val
1

<210> SEQ ID NO 7
<211> LENGTH: 7
<212> TYPE: PRT
<213> ORGANISM: Homo Sapiens

<400> SEQUENCE: 7

Asp Val Gly Ser Asn Lys Gly
1               5
```

```
<210> SEQ ID NO 8
<211> LENGTH: 6
<212> TYPE: PRT
<213> ORGANISM: Homo Sapiens

<400> SEQUENCE: 8

Gly Ser Asn Lys Gly Ala
1               5

<210> SEQ ID NO 9
<211> LENGTH: 5
<212> TYPE: PRT
<213> ORGANISM: Homo Sapiens

<400> SEQUENCE: 9

Arg His Asp Ser Gly
1               5

<210> SEQ ID NO 10
<211> LENGTH: 5
<212> TYPE: PRT
<213> ORGANISM: Homo Sapiens

<400> SEQUENCE: 10

His Asp Ser Gly Tyr
1               5

<210> SEQ ID NO 11
<211> LENGTH: 4
<212> TYPE: PRT
<213> ORGANISM: Homo Sapiens

<400> SEQUENCE: 11

His Gln Lys Leu
1

<210> SEQ ID NO 12
<211> LENGTH: 4
<212> TYPE: PRT
<213> ORGANISM: Homo Sapiens

<400> SEQUENCE: 12

Val Gly Gly Val
1

<210> SEQ ID NO 13
<211> LENGTH: 6
<212> TYPE: PRT
<213> ORGANISM: Homo Sapiens

<400> SEQUENCE: 13

Ser Asn Lys Gly Ala Ile
1               5

<210> SEQ ID NO 14
<211> LENGTH: 5
<212> TYPE: PRT
<213> ORGANISM: Homo Sapiens

<400> SEQUENCE: 14

Val His His Gln Lys
1               5

<210> SEQ ID NO 15
```

```
<211> LENGTH: 5
<212> TYPE: PRT
<213> ORGANISM: Homo Sapiens

<400> SEQUENCE: 15

Gly Ser Asn Lys Gly
1               5

<210> SEQ ID NO 16
<211> LENGTH: 4
<212> TYPE: PRT
<213> ORGANISM: Homo Sapiens

<400> SEQUENCE: 16

Glu Val His His
1

<210> SEQ ID NO 17
<211> LENGTH: 4
<212> TYPE: PRT
<213> ORGANISM: Homo Sapiens

<400> SEQUENCE: 17

Asp Val Gly Ser
1

<210> SEQ ID NO 18
<211> LENGTH: 7
<212> TYPE: PRT
<213> ORGANISM: Homo Sapiens

<400> SEQUENCE: 18

Val Gly Ser Asn Lys Gly Ala
1               5

<210> SEQ ID NO 19
<211> LENGTH: 6
<212> TYPE: PRT
<213> ORGANISM: Homo Sapiens

<400> SEQUENCE: 19

Glu Asp Val Gly Ser Asn
1               5

<210> SEQ ID NO 20
<211> LENGTH: 5
<212> TYPE: PRT
<213> ORGANISM: Homo Sapiens

<400> SEQUENCE: 20

Gln Lys Leu Val Phe
1               5

<210> SEQ ID NO 21
<211> LENGTH: 5
<212> TYPE: PRT
<213> ORGANISM: Homo Sapiens

<400> SEQUENCE: 21

Asn Lys Gly Ala Ile
1               5

<210> SEQ ID NO 22
<211> LENGTH: 5
<212> TYPE: PRT
```

<213> ORGANISM: Homo Sapiens

<400> SEQUENCE: 22

Gly Gly Val Val Ile
1               5

<210> SEQ ID NO 23
<211> LENGTH: 6
<212> TYPE: PRT
<213> ORGANISM: Homo Sapiens

<400> SEQUENCE: 23

Gln Lys Leu Val Phe Phe
1               5

<210> SEQ ID NO 24
<211> LENGTH: 6
<212> TYPE: PRT
<213> ORGANISM: Homo Sapiens

<400> SEQUENCE: 24

Asn Lys Gly Ala Ile Ile
1               5

<210> SEQ ID NO 25
<211> LENGTH: 5
<212> TYPE: PRT
<213> ORGANISM: Homo Sapiens

<400> SEQUENCE: 25

Ser Asn Lys Gly Ala
1               5

<210> SEQ ID NO 26
<211> LENGTH: 5
<212> TYPE: PRT
<213> ORGANISM: Homo Sapiens

<400> SEQUENCE: 26

Val Gly Gly Val Val
1               5

<210> SEQ ID NO 27
<211> LENGTH: 4
<212> TYPE: PRT
<213> ORGANISM: Homo Sapiens

<400> SEQUENCE: 27

Val Phe Phe Ala
1

<210> SEQ ID NO 28
<211> LENGTH: 4
<212> TYPE: PRT
<213> ORGANISM: Homo Sapiens

<400> SEQUENCE: 28

Gly Leu Met Val
1

<210> SEQ ID NO 29
<211> LENGTH: 4
<212> TYPE: PRT
<213> ORGANISM: Homo Sapiens

```
<400> SEQUENCE: 29

Gly Val Val Ile
1

<210> SEQ ID NO 30
<211> LENGTH: 7
<212> TYPE: PRT
<213> ORGANISM: Homo Sapiens

<400> SEQUENCE: 30

Phe Phe Ala Glu Asp Val Gly
1               5

<210> SEQ ID NO 31
<211> LENGTH: 6
<212> TYPE: PRT
<213> ORGANISM: Homo Sapiens

<400> SEQUENCE: 31

Leu Met Val Gly Gly Val
1               5

<210> SEQ ID NO 32
<211> LENGTH: 4
<212> TYPE: PRT
<213> ORGANISM: Homo Sapiens

<400> SEQUENCE: 32

Ile Gly Leu Met
1

<210> SEQ ID NO 33
<211> LENGTH: 4
<212> TYPE: PRT
<213> ORGANISM: Homo Sapiens

<400> SEQUENCE: 33

Asp Ser Gly Tyr
1

<210> SEQ ID NO 34
<211> LENGTH: 6
<212> TYPE: PRT
<213> ORGANISM: Homo Sapiens

<400> SEQUENCE: 34

Asp Val Gly Ser Asn Lys
1               5

<210> SEQ ID NO 35
<211> LENGTH: 9
<212> TYPE: PRT
<213> ORGANISM: Homo Sapiens

<400> SEQUENCE: 35

Ala Glu Asp Val Gly Ser Asn Lys Gly
1               5

<210> SEQ ID NO 36
<211> LENGTH: 6
<212> TYPE: PRT
<213> ORGANISM: Homo Sapiens

<400> SEQUENCE: 36
```

```
Glu Val His His Gln Lys
1               5

<210> SEQ ID NO 37
<211> LENGTH: 6
<212> TYPE: PRT
<213> ORGANISM: Homo Sapiens

<400> SEQUENCE: 37

Val His His Gln Lys Leu
1               5

<210> SEQ ID NO 38
<211> LENGTH: 9
<212> TYPE: PRT
<213> ORGANISM: Homo Sapiens

<400> SEQUENCE: 38

Glu Arg His Val Gly Asp Leu Gly Asn
1               5

<210> SEQ ID NO 39
<211> LENGTH: 9
<212> TYPE: PRT
<213> ORGANISM: Homo Sapiens

<400> SEQUENCE: 39

Arg His Val Gly Asp Leu Gly Asn Val
1               5

<210> SEQ ID NO 40
<211> LENGTH: 4
<212> TYPE: PRT
<213> ORGANISM: Homo Sapiens

<400> SEQUENCE: 40

His Gly Gly Pro
1

<210> SEQ ID NO 41
<211> LENGTH: 4
<212> TYPE: PRT
<213> ORGANISM: Homo Sapiens

<400> SEQUENCE: 41

Leu Val Val His
1

<210> SEQ ID NO 42
<211> LENGTH: 42
<212> TYPE: PRT
<213> ORGANISM: Homo Sapiens

<400> SEQUENCE: 42

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

SYSTEMS AND METHODS FOR PREDICTING MISFOLDED PROTEIN EPITOPES BY COLLECTIVE COORDINATE BIASING

CROSS-REFERENCE TO RELATED APPLICATIONS

This application is a national phase entry of PCT/CA2016/051306, filed Nov. 9, 2016, which claims priority from U.S. Provisional patent application Ser. Nos. 62/253,044 filed Nov. 9, 2015; 62/289,893 filed Feb. 1, 2016; 62/309,765 filed Mar. 17, 2016; 62/331,925 filed May 4, 2016; 62/352,346 filed Jun. 20, 2016; 62/363,566 filed Jul. 18, 2016; 62/365,634 filed Jul. 22, 2016; and 62/393,615 filed Sep. 12, 2016; each of these applications being incorporated herein in their entirety by reference.

INCORPORATION OF SEQUENCE LISTING

A computer readable form of the Sequence Listing "P55846US01_SequenceListing.txt" (5,671 bytes), submitted via EFS-WEB and created on May 9, 2018, is herein incorporated by reference.

TECHNICAL FIELD

The invention relates to prediction of misfolded protein epitopes, more precisely unfolding-specific protein epitopes. Unfolding-specific epitopes can arise when a protein has lost at least some of its structure. Misfolded proteins may present such epitopes, while properly folded proteins will not. Particular embodiments provide methods for predicting misfolded protein epitopes which comprise: conducting molecular-dynamics-based simulations that impose a collective coordinate bias (e.g. a globally imposed collective coordinate bias) on a protein (or peptide-aggregate) to force the protein (or peptide-aggregate) to unfold; and then predicting unfolded protein epitopes based on detection of unfolded regions within the partially unstructured proteins (or peptide aggregates) resulting from the simulations.

BRIEF DESCRIPTION OF DRAWINGS

Exemplary embodiments are illustrated in referenced figures of the drawings. It is intended that the embodiments and figures disclosed herein are to be considered illustrative rather than restrictive.

FIGS. 6A-6D (collectively FIG. 6) show several "fireplots" for different Aβ fibril structures, which illustrate the analysis of potential candidate epitopes and prediction of candidate epitopes based on the output of the biasing process applied in the method of FIG. 1 according to a particular embodiment.

FIG. 7 shows fireplots for several time periods during and after biasing, for the 3-fold symmetric structure 2M4J. FIG. 7A corresponds to a 1 ns time window centered on 4 ns; similarly FIG. 7B corresponds to 1 ns time window centered on 8 ns; FIG. 7C, 12 ns; FIG. 7D, 16 ns; and FIG. 7E, 20 ns. The system is only biased to Q=0.6 (see FIG. 3), so both panels 7D and 7E correspond to Q=0.6.

FIG. 12 is a rendering of the Aβ42 structure 2MXU after biasing to 0.8 of initial Q.

FIG. 16 is a series of plots showing the removal of candidate epitopes and sub-epitopes from the FIG. 6A fireplot as a part of the method of FIG. 5C according to a particular embodiment.

DESCRIPTION

Figure 1:
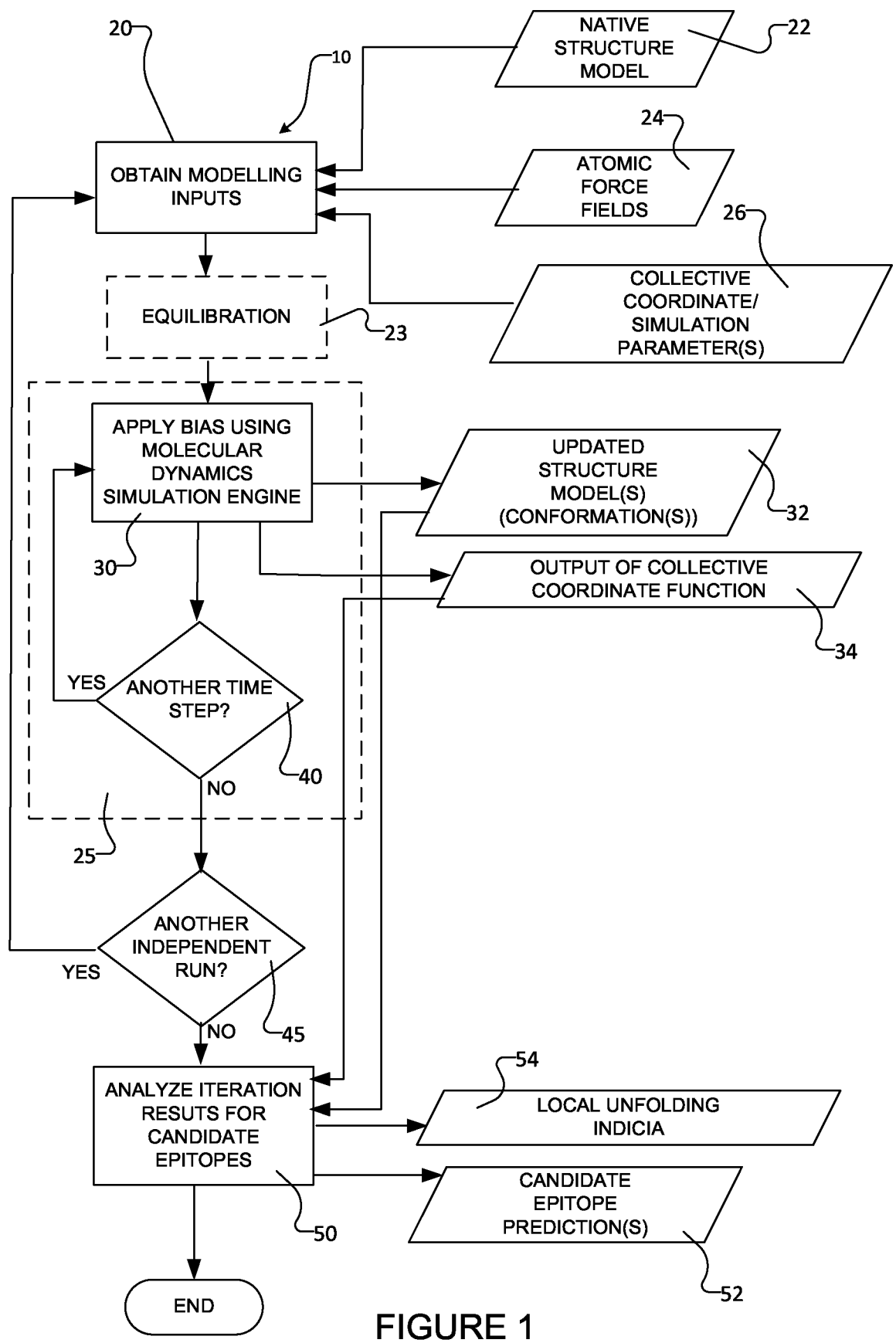
FIG. 1 schematically depicts a computer-based or computer-implemented method for predicting candidate misfolded protein epitopes according to a particular embodiment.

Throughout the following description, specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Aspects of this disclosure provide methods and systems for prediction of misfolded protein epitopes. Proteins, or peptide aggregates, typically exhibit so-called native structure or fibril structure respectively. This disclosure refers to both native structure and fibril structure as the "native structure" when it is clear from the context. Typically, the native structure of a protein is stabilized by interactions (referred to as contacts) between various parts of the protein. Particular embodiments provide methods for predicting unfolding-specific protein epitopes which comprise conducting molecular-dynamics-based simulations which impose a collective coordinate bias on a protein (or peptide-aggregate) to force the protein or peptide-aggregate to unfold. In this disclosure and the accompanying claims, unless the context dictates otherwise, a collective coordinate (or collective variable) corresponding to a protein or peptide aggregate is a variable that is based on a plurality of parameters/variables of a molecular-dynamics based model corresponding to the protein or peptide aggregate. The collective coordinate may be global to the protein or peptide aggregate under consideration. In this disclosure and the accompanying claims, unless the context dictates otherwise, a global collective coordinate (or for brevity a global coordinate) refers to a collective coordinate that depends on the parameters/variables associated with the atoms of a model (e.g. a molecular-dynamics based model) corresponding to at least a substantial portion of the protein or peptide aggregate without selection, weighting or the like of the parameters/variables corresponding to any sub-portion of the substantial portion of the protein or peptide aggregate based on geometrical/spatial criteria associated with the atoms, the location(s) of the atoms in the primary sequence, the secondary structure of particular atoms or the like. The substantial portion of the protein or peptide aggregate may comprise all of the protein or peptide aggregate or all but the boundary structure, as meant to apply to appropriate boundary conditions (e.g. edge residues or edge peptide chains) of the protein or peptide aggregate. A non-limiting example of a global collective coordinate would involve the root mean squared deviation (RMSD) in the positions of all the alpha-Carbon atoms in a protein structure relative to the corresponding positions in the native structure. Two non-limiting examples of collective coordinates that are local rather than global would be the following: 1) the RMSD in the positions of all the alpha-Carbon atoms that are only within the hydrophobic core of the protein, 2) the RMSD of only the alpha-carbons that are in the turn regions of the secondary structure. Both of these examples have additional restrictive conditions on the selection of the atoms that have taken into account a priori information about select parts or subsets of the native or fibril structure, whereas the global coordinate above does not utilize any a priori biased weighting on sub-portions of the native structure.

After imposing the collective coordinate bias which forces the protein or peptide aggregate to unfold, methods according to some aspects of the invention comprise predicting unfolded protein epitopes based on detection of unfolded regions of the partially unstructured (i.e. not natively structured or fibrillary structured) protein or peptide aggregate which result from the simulations. In some embodiments, a globally applied collective coordinate bias forces the protein or peptide aggregate to have fewer or different contacts than in the native structure, while allowing the protein to adopt its own misfolded (non-native) structure in response to the globally applied collective coordinate bias or, if no non-native contacts are adopted by the disrupted protein system, to unfold in some regions preferred by the energy function of the protein.

Some aspects of this disclosure provide computer-based systems and methods for identifying one or more epitopes unique to a protein or set of proteins or peptide chains exhibiting partial local unfolding from a native structure or aggregated structure. As is understood, aggregated structures (also referred to as peptide aggregates or fibrils) comprise pluralities (e.g. 3, 5, 10, 100 or 1000) of peptide chains, including possibly proteins, which aggregate (e.g. at relatively high concentrations). While the individual peptide chains that form an aggregate structure may or may not have their own native structures, the aggregated structure typically has one or more "native" fibril structures which may depend on peptide chains involved, the conditions under which the peptide chains aggregate and possibly on stochastic factors, such as, by way of non-limiting example, random conformations of individual peptide chains. In this disclosure and the accompanying claims, unless the context dictates otherwise, proteins, peptide-aggregates, fibrils and aggregated structures may be referred to herein as proteins and the native structures of proteins, peptide-aggregates, fibrils and/or aggregate structures may be referred to herein as native structures, without loss of generality.

In accordance with some aspects and embodiments of the invention, methods are provided wherein a molecular dynamics-based or Monte-Carlo sampling-based model of a protein is induced to partially disorder from its native structure by biasing (e.g. increasing, decreasing or otherwise varying or manipulating) an externally applied (target) collective coordinate. In some aspects or embodiments, the collective coordinate is a global collective coordinate. In some aspects or embodiments, the collective coordinate is indicative of (e.g. correlated with, a function of, capable of quantifying, capable of ordering or otherwise indicative of) a degree of similarity to the native structure and/or a degree of deviation from the native structure. Non-limiting examples of global collective coordinates include variables based on: a number of stabilizing interactions (contacts) between heavy (non-hydrogen) atoms of the protein (or peptide aggregate) of any particular protein structure from among the contacts in the native structure; a number of stabilizing interactions (contacts) between hydrogen atoms in any particular protein structure from among the contacts between hydrogen atoms in the native structure; distances between all heavy atoms of a particular protein structure relative to the distances between the heavy atoms in the native structure; the root-mean square structural deviation (RMSD) of a particular protein structure relative to the RMSD of its native structure, as defined through the position of the alpha carbon atoms; the RMSD of a particular protein structure relative to its native structure, as defined through the position of the heavy atoms; the total solvent accessible surface area (SASA) of a particular protein structure relative to its native structure; the number of backbone hydrogen bonds in a particular protein structure from among the number of backbone hydrogen bonds in the native structure of the protein; combinations of the foregoing; and/or the like.

Some aspects and embodiments of the invention involve biasing an externally applied (target) collective coordinate and forcing the molecular dynamics-based model of the protein to reorganize its structure to conform to the biased target collective coordinate. Forcing the molecular dynamics-based model to reorganize its structure to conform to the biased target collective coordinate may be accomplished, for example, by forcing the molecular dynamics-based model to minimize a cost function (also referred to as a biasing potential function), where the cost function may depend on a difference between the actual collective coordinate (determined from the molecular dynamics-based model) and the biased target collective coordinate. Forcing the molecular dynamics-based model to reorganize its structure to conform to the biased target collective coordinate may be referred to as applying or imposing a biasing potential or applying or imposing a collective coordinate bias.

Where the applied biasing potential is based on a global collective coordinate, the protein typically does not lose its native structure homogeneously, but instead will lose its native structure (i.e. unfold and possibly misfold) in specific region(s) that are thermodynamically the most prone to disorder. Such region(s) may correspond to those region(s) having relatively weak free energy of stabilization compared to other regions of the protein. The region(s) that disorder upon application of the global biasing potential may comprise misfolding-specific or unfolding-specific epitopes—i.e. epitopes present only in the absence of native structure (e.g. present in the unfolded or misfolded structure, but not present in the native structure) for those region(s).

Aspect of the invention involve the application of collective coordinate bias to structural models of proteins which transforms the structural protein models to exhibit partially unfolded structures that are different from their native structures. The transformation based on collective coordinate bias may be applied globally to at least a substantial portion of the protein model in such a way that bias and corresponding transformation are impartial as to where, within the substantial portion of the protein model, unfolding occurs. The transformed (partially unfolded) structural protein model may then be analyzed to detect indicia of localized unfolding and to identify candidate epitopes, where the candidate epitopes exhibit indicia of localized unfolding.

Aspects of this disclosure provide systems and methods for predicting misfolding-specific, or additionally or alternatively, oligomer-specific, epitopes for a variety of amyloidogenic, neurodegenerative diseases including Alzheimer's disease, ALS, transthyretin amyloid polyneuropathy, as well as partially unfolded, cancer cell-specific epitopes including cell surface receptors such as epidermal growth factor receptors (EGFR), death receptors, and cluster of differentiation proteins. Specific and non-limiting example epitopes predicted in accordance with the systems and methods disclosed herein in aged or disrupted Aβ fibril include, without limitation: residues 13-18 or sequence HHQKLV (SEQ ID NO: 1); residues 6-9 or sequence HDSG (SEQ ID NO: 2), residues 13-16 or sequence HHQK (SEQ ID NO: 3), residues 15-18 or QKLV (SEQ ID NO: 4), residues 21-24 or AEDV (SEQ ID NO: 5), and residues 37-40 (specifically in Aβ42) or GGVV (SEQ ID NO: 6). Antibodies will target these epitopes based on both their sequence identity, and their conformation. Segments of primary sequence that have unfolded from the native structure or fibril are conformationally distinct from corresponding segments in the context of the native structure or fibril. Antibodies targeting such regions will not be raised to the native structure or fibril, but will be raised to peptide scaffolds of the foregoing primary sequences that mimic the unfolded structural ensemble. Antibodies that bind to unfolding-specific epitopes (i.e. that are selected based on the criterion that they unfolded from the fibril upon external perturbation) will not bind to the epitope in the context of the native structural conformation, but will only bind to epitope when it is unstructured. If antibodies are raised to a cyclic peptide, then they may also be selective against the unfolded, monomeric form of the peptide chain, for example selective against monomeric Aβ42.

Some misfolded proteins implicated in both neurodegenerative and systemic amyloid-related diseases appear to exhibit fibrils with a significant degree of native structure, including, by way of non-limiting example, transthyretin, β2-microglobulin, and superoxide dismutase. Such exhibition of fibrils with a significant degree of properly folded, putative-native structure suggests that local, rather than global protein unfolding may play a significant role in these diseases.

Other neurodegenerative diseases appear to involve the aggregation of intrinsically disordered peptides, such as Aβ peptide in Alzheimer's disease, and α-synuclein in Parkinson's disease. However, plaques (i.e. collections of fibrils) predominantly comprising Aβ peptide and neurofibrillary tangles predominantly comprising τ-protein occur with advanced age in most individuals, without any presentation of dementia. On the other hand, intracerebral injection of mice with dilute brain extracts containing Aβ seeds have been observed to induce the phenotypic symptoms of Alzheimer's disease, including plaque deposition and cerebral Aβ angiopathy. Such evidence points to the toxicity of heterogeneous sera of Aβ that may contain oligomers of various size and polymorphic structure, but to the relatively inert function of large fibrils acting by themselves. These findings are consistent with those in prion biology wherein oligomers of prion protein rather than fibrils have been found to be most infectious. Large fibrils may then play a protective role by sequestering Aβ peptide.

In the presence of Aβ monomers however, fibrils can act as nucleation substrates for oligomeric growth and spread. This "secondary nucleation" process has been found by kinetic studies using S-radiolabelled peptides to be dominant source of toxic oligomeric species, more so than direct nucleation between Aβ monomers or fibril fragmentation. Together the above evidence suggests that fibrils may present interaction sites that have the propensity to catalyze oligomerization, but that this may be strain-specific, and may only occur when selective fibril surface not present in normal patients is exposed and thus able to have aberrant interactions with the monomer (i.e. is presented to the monomer). Environmental challenges such as low pH, osmolytes present during inflammation, or oxidative damage may induce disruption in fibrils that can lead to exposure of more weakly-stable regions. There is an interest, then, to predict these weakly-stable regions, and use such predictions to rationally design therapeutics that could target them.

In the context of cancer, there are several lines of evidence that mutation or deletion-induced misfolding of proteins can play a role, either by destabilizing proteins involved in pro-apoptotic pathways, or by altering the function of cell-surface proteins such as growth factors so that they are constitutively active. The presence of molecular crowding, low pH, and reactive oxygen species all contribute to an anomalous environment that will destabilize protein structure, rendering proteins in neoplastic cells prone to more frequent structural disruption.

Misfolded proteins in the context of a neoplasm may present cancer cell-selective antigenic targets; antibodies directed against these targets, rather than against the native protein, may avoid unwanted side effects due to unintentional targeting of folded protein(s) in healthy tissue. Native antibody therapies to EGFR, for example, may antagonize EGF signaling in healthy tissue: the majority (45-100%) of patients receiving EGFR inhibitors develop a papulopustular rash, a smaller fraction develop paronychia and mucositis, and a small number develop severe reactions with life-threatening superinfection of skin lesions. An ideal antibody-based antineoplastic may avoid these adverse reactions by selectively antagonizing EGFR signaling in tumor tissue while sparing EGFR in normal tissue.

In the context of Alzheimer's disease, the above evidence motivates the general desire for prediction of locally-disordered regions of Aβ fibril that may act as "hot-spots" for secondary nucleation, or recruitment sites of Aβ monomer. Regions likely to be disrupted in the fibril may also be good candidates for passively exposed regions in toxic, oligomeric species. As well, the fact that natively-folded proteins may retain a significant degree of native structure when aggregating motivates the prediction of regions in the natively folded structure that are prone to disorder and to thereby lose their native structure, and may act as candidate regions for intermolecular non-native interactions. In the context of cancer, the disruptive influence of the anomalous environment in neoplastic cells provides motivation to predict locally-disordered regions of proteins disregulated in cancer, which may act as cancer-cell specific targets for small molecule or antibody therapies.

Aspects of this disclosure provide computer-based systems and methods to predict contiguous protein regions (epitopes) that are prone to disorder. Specific example epitope predictions based on partially-disrupted Aβ fibrils are described in more detail below.

Force fields parameterized quantum-mechanically (e.g. using a molecular dynamics model (also known as a molecular dynamics engine), such as, by way of non-liming example, CHARMM (Chemistry at HARvard Macromolecular Mechanics, http://www.charmm.org/) and/or the like are now sufficiently accurate to reproduce experimental folded protein structures de novo (i.e. to fold proteins). The force-fields used to fold proteins that are parameterized by quantum chemical computer representations tend to be the most accurate near or around the proteins' respective native structures. Some embodiments of the invention apply the techniques described herein within such contexts (i.e. near or around the native structure) or in relation to partial structural perturbations from this native structure (e.g. the native structure with thermal motion). Hence the known force-fields used in the molecular dynamics models and used in such embodiments are being applied within their range of validity.

Aspects of this disclosure characterize local unfolding events, in which a protein region deviates structurally from its native structure. Aspects of the invention impose a challenge (based on some anomalous environmental queue) to a molecular dynamics based model of a structured protein, such that, in response, the protein begins to unfold or misfold. To effect such techniques, aspects of this disclosure employ a technique referred to herein as collective coordinate biasing, which involves biasing (e.g. increasing, decreasing or otherwise varying or manipulating) an externally applied (target) collective coordinate to apply a corresponding biasing potential to the molecular dynamics based protein model. Once the protein begins to unfold, methods according to some aspects of the invention comprise predicting unfolded protein epitopes based on detection of unfolded regions of the partially unstructured protein.

FIG. 1 depicts a computer-based or computer-implemented method 10 for predicting candidate epitopes 52 (e.g. candidate unfolded epitopes) according to a particular embodiment. Method 10 commences in block 20 which comprises obtaining modelling parameter inputs which may be used to perform method 10. For example, in the illustrated embodiments, the block 20 modelling parameter inputs include, without limitation, native structural model 22, atomic force fields 24 and collective coordinate bias parameters 26. Such modelling parameter inputs 22, 24, 26 may generally be obtained by any suitable technique from any suitable source. In some embodiments, some or all of modelling parameter inputs 22, 24, 26 may be provided to a computer performing method 10 by a user (e.g. through a graphical user interface, command line interface, a network interface, an I/O interface or other suitable interface (e.g. suitable molecular dynamics engine software, and/or the like)). In some embodiments, method 10 may be a part of a more comprehensive computer-based molecular dynamics engine comprising software and/or hardware and some or all of modelling parameter inputs 22, 24, 26 may be determined by the molecular dynamics engine in other routines (not shown). In some embodiments, some or all of modelling parameter inputs 22, 24, 26 may be provided by external systems (e.g. molecular dynamics systems, databases and/or the like implemented on computers in communication with the computer performing method 10. In some embodiments, some of modelling parameter inputs 22, 24, 26 may be derived from other modelling parameter inputs 22, 24, 26 (e.g. in steps of method 10 not expressly shown in FIG. 1).

In the illustrated embodiment, block 20 comprises obtaining a structural model 22 of the protein to be subjected to the method (e.g. a protein which may be implicated or otherwise considered to be associated with a particular disease). Structural model 22 may comprise a computer representation of the subject protein suitable for use with the molecular dynamics engine which performs block 30 (discussed in more detail below). Structural model 22 and its associated computer representation may specify (in a suitable manner) the physical coordinates (e.g. the x, y and z physical locations) of the nuclei of the atoms in the protein under consideration. Unless the context dictates otherwise, in this disclosure and the accompanying claims, the term structure when applied to a protein (e.g. a protein under consideration in method 10) should be understood to correspond to the physical coordinates (e.g. the x, y and z physical locations) of some or all of the nuclei of the atoms in the protein and/or to some computer representation of such physical coordinates. Structural model 22 obtained as a part of the block 20 modelling parameter inputs may provide, dictate or express the "native" structure for the protein under consideration, which may be subject to a collective coordinate bias by the simulation performed in block 25 to provide updated structure models 32, as described in more detail below. Structural model 22 may comprise an experimentally-determined set of nuclear coordinates or may be determined computationally. In some embodiments, structural model 22 may be obtained from the protein data bank (PDB, such as that available at www.rcsb.org). In some embodiments, structural model 22 obtained as a part of the block 20 modelling parameter inputs may comprise a computer-based representation of a properly folded native protein structure, or it may comprise a computer-based representation of a misfolded and aggregated fibril structure. Structural model 22 may comprise a single protein chain or a plurality of peptide chains which may form aggregated structures (e.g. fibrils). As discussed above, for the sake of brevity, proteins and aggregated structures subjected to method 10 may be referred to in this disclosure and the accompanying claims as a protein or proteins, without loss of generality.

Block 20 also involves obtaining computer representations of the atomic force fields 24 associated with the protein under consideration. Such atomic force fields 24 may be configured for use with the form of the computer representation of structural model 22 and/or the molecular dynamics engine which performs block 30. Force fields 24 may comprise parameterized force field models, such as those provided by CHARMM or similar force field models, such as OPLS (Optimization Potentials for Liquid Simulations), GROMOS (www.gromos.net) and/or the like, which are usable by a corresponding molecular dynamics engine to simulate the structure of a protein. In some embodiments, structural model 22 and atomic force fields 24 may be integrated.

In the illustrated embodiment, block 20 also comprises obtaining collective coordinate and/or simulation parameters 26 which describe how an externally applied target collective coordinate will be biased (e.g. increased, decreased or otherwise varied or manipulated) during the block 25 simulation loop described in more detail below. For example, such collective coordinate bias parameters 26 may specify the rate of change of the target collective coordinate, the amplitude of the change of the target collective coordinate, the maximum and/or minimum value of the target collective coordinate, other parameters of the biasing potential function, such as, by way of non-limiting example, the rigidity (or "spring-constant") k of the potential function described below and/or the like. Parameters 26 may additionally or alternatively include other simulation parameters of the simulation to be performed in block 25, such as, by way of non-limiting example, the duration and/or time step discretization like of the simulation, the duration of the simulation, and/or the like. In some embodiments, the simulation may force a protein to unfold using metadynamics which involve penalizing conformations similar to those that have already been explored—see, for example, Bonomi et al. PLUMED: A portable plugin for free-energy calculations with molecular dynamics, *Computer Physics Communications* 180 (2009) 1961-1972, which is hereby incorporated herein by reference. In some such embodiments, parameters of the metadynamics may be part of simulation parameters 26.

After having obtained the modelling parameter inputs in block 20, method 10 proceeds to a simulation loop 25 comprising, in the illustrated embodiment, blocks 30 and 40. In some embodiments, the block 50 analysis step shown in FIG. 1 may be performed in whole or in part inside of loop 25. The loop 25 simulation may be implemented by a molecular dynamics engine and may comprise a computer-implemented discrete time simulation involving times steps on the order of femtoseconds (i.e. 1 fs=$10^{-15}$ s) or even fractions of femtoseconds. The loop 25 simulation may be implemented by a software molecular dynamics engine running on a suitable computer or plurality of computers. A number of software molecular dynamics engines are known in the art. In one particular embodiment, the block 25 loop is performed using the publically-available software packages GROMACS and PLUMED, as updated from time to time. As part of the block 25 simulation loop, a collective coordinate bias potential is applied to the protein which forces a transformation of the structural model 22 obtained as input in block 20 to generate updated structural model (also referred to as an updated conformation) 32 of the protein under consideration. Moreover, the structural model of the protein under consideration is transformed during each time step of the block 25 simulation to generate updated structural models (or conformations) 32 of the protein. Specifically, the structure of the protein (i.e. the computer representations of the physical coordinates of the nuclei of the protein's atoms) is transformed during each time step to generate an updated structural model 32.

As will be discussed in more detail below, the loop 25 simulation comprises applying a collective coordinate bias to the protein under consideration and observing the protein over a series of time steps. A global collective coordinate may comprise any suitable function of the atomic positions (e.g. the physical coordinates of the nuclei) and/or the energies which, when biased, applies a globally destabilizing influence to the protein under consideration, thereby inducing loss of native structure. Non-limiting examples of global collective coordinates have been described above.

Updated structural model(s) 32 (also referred to as conformation(s) 32) may refer to the transformed structure(s) of the computer representation of a protein under consideration after one or more iterations of loop 25. In some embodiments, a new conformation 32 is generated in each iteration (e.g. for each time step) of loop 25, in which case conformation(s) 32 shown in FIG. 1 may actually comprise a plurality of conformations 32. In some embodiments, loop 25 also generates a collective coordinate output 34 in each iteration (e.g. for each time step). The collective coordinate output 34 for any conformation 32 may be determined, for each time step, based on updated structural models 32 of the current and/or previous time steps. The collective coordinate output 34 may comprise the "actual" collective coordinate of the protein under consideration at a particular time step (in contrast to the externally applied "target" collective coordinate. In some embodiments, collective coordinate output 34 for any time step or any corresponding conformation 32 may comprise a parameter which is correlated with, a function of and/or otherwise indicative of a degree of native structure present for that conformation 32 or a lack of degree of native structure (e.g. unfolding) present for that conformation 32. In some embodiments, the collective coordinate output 34 is a scalar. For example, the collective coordinate output 34 may be in a range [0,1], such that a fully-native structure (e.g. a structure obtained as native structure model 22 from a PDB in block 20) may have a global coordinate output 34 of unity, while in a globally unfolded, random coil structure, collective coordinate output 34 may have a value at or near zero.

The collective coordinate biasing methods used in method 10 and loop 25 or otherwise described herein may be used to demand (at least approximate to within an acceptable threshold) particular levels of global unfolding from a candidate protein without specifying how or where (within the protein structure) that unfolding is to occur. For example, the collective coordinate may be a global collective coordinate, such that when used to bias the protein under consideration, the global collective coordinate merely requires that the protein achieve global unfolding to track a target collective coordinate while allowing the protein to adopt any local unfolding to achieve the global target. By demanding that a protein is, say, 30% unfolded (and thus 70% folded), method 10 may be used to analyze and draw results from an equilibrium protein structure constrained to be 30% partially-disordered. Where the collective coordinate bias is global (e.g. towards a structure with 30% disorder), the global collective coordinate bias does not specify where or how the protein may become locally disordered to satisfy the 30% disorder constraint. The region(s) of disorder may be adopted by the protein based on the protein's internal energy function or force field (i.e. based on the computer based model representation of the protein) and the requirement that the protein satisfy the collective coordinate bias constraint. As described in more detail below, the localized regions or "hot-spots" of the protein that are prone to becoming disordered (e.g. as may be determined from local unfolding indicia 54 in the illustrated embodiment) may be analyzed in block 50 to provide the method 10 candidate epitope predictions 52. These method 10 candidate epitopes 52 may then serve as antigenic targets, to which therapeutic agents may be designed.

Candidate epitope predictions 52 based on method 10 may be as accurate as the input force fields 24 and computer-based model representations 22 used for the loop 25 simulation. As mentioned above, distributed computing or custom supercomputers can now accurately fold proteins using these force-fields, which supports the accuracy of the force field models 24 and computer-based model representations 22 used as the block 20 inputs to method 10.

An input computer-based structural model 22 (e.g. as obtained from a PDB in block 20) may comprise a set of three dimensional coordinates for all atoms of the protein. Where the input computer-based structural model 22 is a native structural model, it defines a set of native contacts (also referred to herein as initial contacts). A set of initial contacts may be defined to include all (or a set of) pairs of heavy (other than hydrogen) atoms in the native structure model 22 having nuclei which are within a threshold distance (e.g. 4.8 A° or some other suitable distance) of each other. A typical PDB native structure 22 for a protein with primary sequence of length on the order of 100 amino acids may typically have about 2000 initial contacts or thereabouts. In some embodiments, the number of contacts may represent a global collective coordinate used in method 10. In such embodiments, the number of initial contacts may represent the initial value of the actual collective coordinate of the protein under consideration (prior to any iterations of simulation loop 25).

In some embodiments, rather than using a strictly native structure in loop 25, an input protein structure 22 may be equilibrated using an optional equilibrating process 23 (shown in FIG. 1 with dashed lines). Equilibration process 23 may comprise a simulation that allows the protein under consideration to come to equilibrium in an external environment characterized by typical thermodynamic variables that are well-known to practitioners in the art. Such thermodynamic variables may include, but are not limited to, a constant number of particles, constant pressure, and constant temperature and/or the like. In addition or in the alternative, equilibration process 23 may be achieved with a constant number of particles, a constant system volume, and a constant temperature and/or the like. Where a protein is equilibrated in block 23 prior to commencing simulation loop 25, the equilibrated structure (i.e. the computer representation of the equilibrated structure) may be used (in addition to or in the alternative to input protein structure 22 or to the true native structure) to determine the initial contacts for the protein under consideration and for the input to the first iteration of simulation loop 25. Typically, an equilibrated protein may have a slightly smaller number of initial contacts (as compared to a PDB native structure), since some weakly stable contacts may be broken simply due to thermal fluctuations during the block 23 equilibration process. In some embodiments, the block 23 equilibration process is not used. In some embodiments, the input structural model 22 obtained in block 20 is already equilibrated. Unless the context dictates otherwise, references to a native structure described herein may be considered to include an equilibrated structure. Where a structure is equilibrated, the native structure 22 used in the remainder of method 10 may be obtained in block 20 by suitable averaging over a number of time steps (e.g. a stochastic ensemble relating to the protein in thermal equilibrium) to accommodate stochastic variation within its allowable conformational space. Unless the context dictates otherwise, references to the native structure of an equilibrated protein may refer to this average native structure.

In some embodiments, for proteins comprising multiple chains (e.g. aggregated structures), method 10 (FIG. 1) may include both inter-chain and intra-chain contacts in the determination of the number of initial contacts and/or in the determination of the collective coordinate output 34 (i.e. the actual value of the collective coordinate in each iteration of simulation loop 25).

Figure 2:
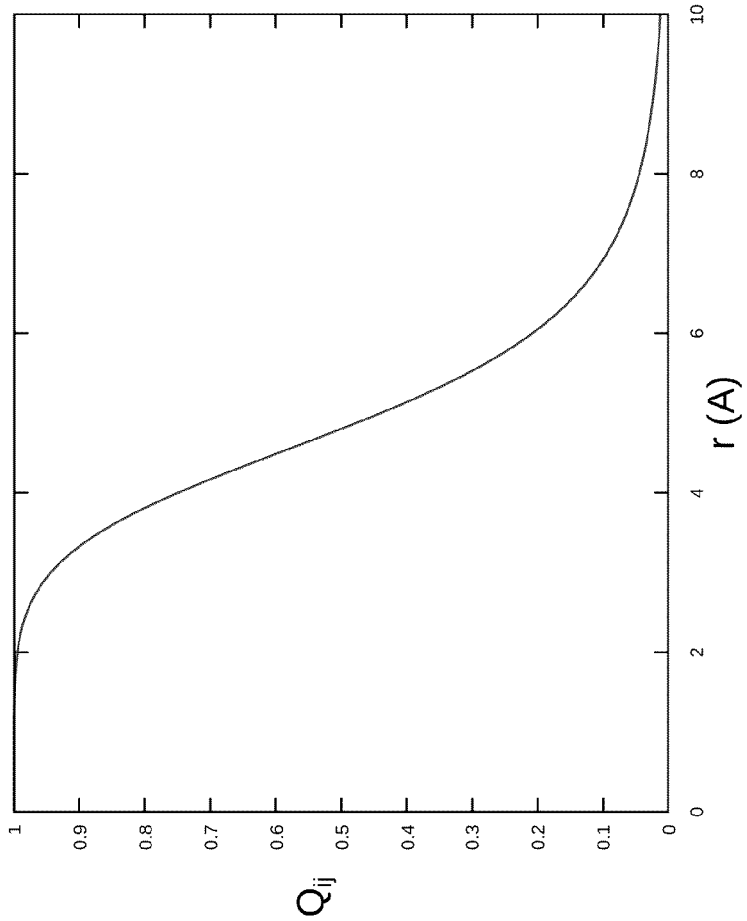
FIG. 2 shows a plot of the equation (1) contact function $Q_{ij}(r)$ versus distance r for an exemplary contact.

In some embodiments, method 10 uses a set of contacts (or a representation of the set of contacts) as a basis for the collective coordinate used force a protein to unfold during the loop 25 simulation. More specifically, in some embodiments, the collective coordinate used for biasing a protein comprises the number of contacts from among a set of initial contacts. An exemplary embodiment using a representation of the set of contacts as a collective coordinate is described below, without loss of generality that the collective coordinate may have other forms. A representation of the initial set of contacts for the loop 25 simulation may generated from input (e.g. native) structure model 22 of the protein under consideration obtained in block 20 and/or from an equilibrated version of the protein under consideration obtained as output of the block 23 equilibration process. A representation of the number of contacts from among the initial set of contacts (and the corresponding collective coordinate output 34 or actual value of the collective coordinate) at any later time step may be determined from the updated structural model 32 in a similar manner. For each heavy atom pair (indexed by ij) in the protein structure under consideration, method 10 may comprise the use of a native contact function $Q_{ij}(r)$. In some embodiments, the contact function $Q_{ij}(r)$ may comprise a function of the atom pair ij and the distance $r_{ij}$ between the atoms of the pair ij. In one particular embodiment, the contact function $Q_{ij}(r)$ has the form:

$$Q_{ij} = \frac{1 - \left(\frac{r_{ij}}{r_0}\right)^n}{1 - \left(\frac{r_{ij}}{r_0}\right)^m} \quad (1)$$

where $r_{ij}$ is the distance between the nuclei of atoms i and j in the protein under consideration. The other equation (1) parameters $r_0$, n and m may be suitably selected constants. In some embodiments, m>n. In one particular embodiment, $r_0$=4.8 A° (Angstrom), n=6, and m=12. FIG. 2 shows a plot of the equation (1) contact function $Q_{ij}(r)$ versus distance r for an exemplary contact. As will be explained in more detail below, the smooth form of the contact function $Q_{ij}(r)$ allows for a collective coordinate Q, which can used to formulate a potential function V where the potential function V may be conveniently converted to forces which may in turn be used by the molecular dynamics engine. Since $Q_{ij}(r)$ is always less than one (while asymptotically approaching 1 as r→0), the sum $Q=\Sigma Q_{ij}$ (summed over every pair of atoms in the protein structure under consideration) is nearly always less than the total number of contacts in the native structure. The structural model used to define the set of contacts may be referred to as the initial structure, and the sum over contacts in this structure may be referred to as $\Sigma_{ij}^{initial}$. States that deviate from this initial structure, either because of thermal fluctuations or because of biasing forces, will generally have a fraction of the initial contacts less than unity. In practice, it may not be necessary to calculate $Q_{ij}$ for all pairs ij of atoms—e.g. a thresholding process may be used to set $Q_{ij}=0$ for some pairs ij of atoms that are very far apart. As discussed above, the collective coordinate in some embodiments may be based on heavy atoms and/or particular heavy atoms rather than all of the atoms in protein. For example, collective coordinates may be based on all of the carbon atoms in a protein or all of the alpha carbon atoms in a protein.

There are many functions that have a similar functional form and/or functional characteristics as that of equation (1) shown in FIG. 2. Method 10 may use any such function (e.g. where the function goes from 1 to 0 as r goes from zero to ∞ and having a characteristic length scale of $r_0$) as a contact function $Q_{ij}(r)$. The parameters for $r_0$, n, and m (e.g. in equation (1)) may be selected to characterize a continuous function with the approximate range of physical hydrogen bonding interactions in the protein.

Some embodiments may use a continuous contact function (e.g. the equation (1) contact function) to weight contacts (rather than, for example, a Heaviside or discrete step function), because, as explained in more detail below, it may be desirable to apply a biasing potential as a function of $Q_{ij}$ during the loop 25 simulation, where such a potential is implemented as a force (e.g. the derivative of the potential) on individual atom positions. Thus, in some embodiments, it is desirable for $Q_{ij}$ to be a differentiable function of r with a well-defined derivative. In some embodiments, a discrete function, such as a Heaviside step function or multiple step variation of on a step function, may be used to describe native contacts. Such a formulation may be amenable to discrete molecular dynamics (DMD) simulation protocols, which generally use step-wise potential functions for inter-atomic interactions.

An actual collective coordinate Q (e.g. collective coordinate output 34 in method 10) for any structure characterized by the set of pairwise distances between heavy atoms (non-hydrogen atoms) $\{r_{ij}\}$ may then be characterized by the equation:

$$Q = \frac{\sum_{ij}^{initial} Q_{ij}(r_{ij})}{\sum_{ij}^{initial} \langle Q_{ij}(r_{ij}) \rangle} \quad (2)$$

where in equation (2), $Q_{ij}$ is given in equation (1), the sum $\Sigma_{initial}$ is over the pairs of atoms in the input (e.g. native) structure model 22 or from the native structure 22 itself "Initial" in the above equation indicates that the sum is only over those contacts present in the initial native structure (typically a PDB model of the properly folded structure or the fibril structure). In the embodiment described in equation (2) above, the quantity in the denominator of equation (2) is the thermal average of the $Q_{ij}$ values in the input (e.g. native) structure model 22 or the equilibrated structure, and the quantity in the equation (2) numerator is the sum of $Q_{ij}$ in an arbitrary structure (e.g. of the updated structural model 32 obtained in each iteration of the block 25 loop). The brackets <...> in the denominator indicate the equilibrium (thermal) average of the native state, i.e. thermally-occupied structures when running a molecular dynamics simulation starting from the native PDB structure. The quantity Q in equation (2) is typically a number between zero and unity.

Other metrics (e.g. metrics other than equation (2) and/or metrics based on criteria other than contacts) are additionally or alternatively possible to characterize the degree of disorder from a native structure and, consequently, may be used as collective coordinates (e.g. global collective coordinates) in some embodiments. These metrics may comprise, for example, the root mean squared deviation (RMSD) of an updated structure model 32 relative to the native structure model 22, the radius of gyration of an updated structure model 32 relative to the radius of gyration of the native structure 22, the number of backbone hydrogen bonds in the updated structure model 32 from among the backbone hydrogen bonds in the native structure 22, the total solvent-accessible surface area (SASA) of the updated structure model 32 relative to the SASA of the native structure 22, the structural overlap function described by C. J. Camacho and D. Thirumalai. Kinetics and thermodynamics of folding in model proteins. *Proc. Natl. Acad. Sci. USA*, 90(13):6369-6372, 1 Jul. 1993 (which is hereby incorporated herein by reference), the generalized Euclidean distance from the native structure described by A. Das, B. K. Sin, A. R. Mohazab, and S. S. Plotkin, Unfolded protein ensembles, folding trajectories, and refolding rate prediction. *J. Chem. Phys.*, 139(12):121925, 2013 (which is hereby incorporated herein by reference), functions of one or more of these parameters, and/or the like. In some embodiments, each of these collective coordinates used for within a biasing simulation (e.g. simulation loop 25) may be expressed as a scalar Q. For the sake of brevity, this description refers to the use of a single collective coordinate. However, unless the context dictates otherwise, references to a collective coordinate should be understood to include the possibility of combinations of multiple collective coordinates.

In some embodiments, loop 25 of method 10 comprises asserting a bias potential over a series of time steps as a time-dependent potential of the form:

$$V(Q,t) = \tfrac{1}{2}k(Q-Q_c(t))^2 \quad (3)$$

where $Q_c(t)$ is a target collective coordinate which may be user-specified and which may be part of collective coordinate/simulation parameters 26 and where Q is the actual collective coordinate of the updated structural model at any given time step. It can be observed that equation (3) potential function has the appearance of the potential energy function of a spring, where the parameter k is similar to a spring constant. It can also be observed that for k>0, the equation (3) potential function increases where the actual collective coordinate Q differs from the target collective coordinate $Q_c(t)$. The loop 25 simulation may comprise minimizing the potential function (e.g. minimizing equation (3)) to ensure that the actual collective coordinate Q tracks the target collective coordinate $Q_c(t)$. In some embodiments, potential function having other forms which penalize differences between the actual collective coordinate Q and the target collective coordinate $Q_c(t)$ may be used in addition to or in the alternative to equation (3). Equation (3) and other potential functions having similar characteristics may be used for any of the collective coordinates described herein.

Figure 3:
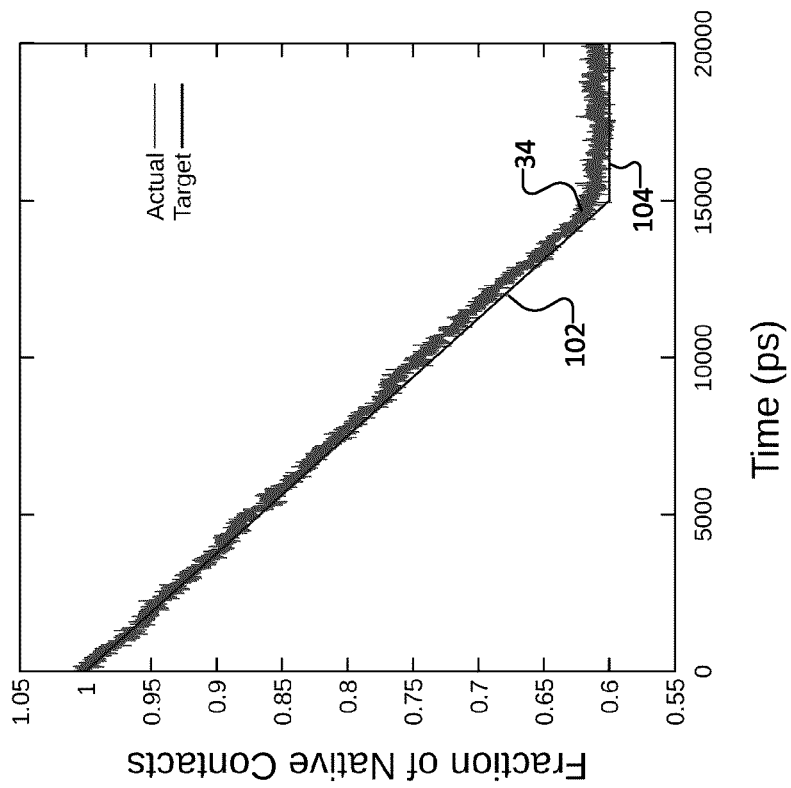
FIG. 3 shows a plot of Q(t), as simulated using the method of FIG. 1, and $Q_c(t)$, a smooth or linear (e.g. constant rate of change) target collective coordinate curve, versus time for a typical biasing simulation of Aβ amyloid.

In some embodiments, the target collective coordinate $Q_c(t)$ may comprise a function of time, which starts at the value of Q for the input (e.g. native) structure (which may typically be unity or close to unity), and decreases with time. In some embodiments, $Q_c(t)$ may decrease linearly at a rate which may be specified by collective coordinate/simulation parameter(s) 26 to some suitable level. In general, the characteristics of the target collective coordinate $Q_c(t)$ may be specified or otherwise configured according to collective coordinate/simulation parameter(s) 26. An exemplary unfolding trajectory of the target collective coordinate $Q_c(t)$ as a function of time, and the actual collective coordinate Q of a protein under consideration (e.g. collective coordinate output 34 for each time step) as a function of time, are shown in FIG. 3. More specifically, FIG. 3 shows a plot of an example actual collective coordinate Q(t) (e.g. collective coordinate output 34 as simulated using method 10) and a smooth target collective coordinate curve ($Q_c(t)$) 102 which may be provided by output collective coordinate 34 at each time step) versus time for a typical biasing simulation of Aβ amyloid.

The potential V(Q,t) in equation (3) may be implemented (in block 30 of loop 25) by adding this potential to the total energy of the protein under consideration. The protein will try to minimize its free energy, but it will take time to do so; this is one reason for the lag between the target collective coordinate $Q_c(t)$ 102 and the actual collective coordinate Q(t) 34 of the protein exhibited in FIG. 3. Another reason for the lag exhibited in FIG. 3 is because there is a non-zero residual force present when the protein under consideration is perturbed from its native structure, which results in a difference in the new equilibrium value of the actual collective coordinate Q 34 of the protein that is slightly different from the target collective coordinate $Q_c$ in the presence of the potential V.

If the rate of decrease of the target collective coordinate $Q_c$ 102 is too rapid, the values of the actual collective coordinate Q 34 characterizing the protein under consideration may deviate substantially from the value of the target collective coordinate $Q_c$ 102, and the perturbation on the protein due to V(Q,t) will induce a highly non-equilibrium unfolding process. Some embodiments attempt to maintain a quasi-equilibrium (adiabatic) process as the protein unfolds. The rate of decrease for the target collective coordinate $Q_c(t)$ 102 may, in some embodiments, be determined by a condition that the actual collective coordinate Q 34 is not too far different from the target $Q_c$ 102. Such a slow (adiabatic) perturbation yields an unfolding process that is governed primarily by the interactions within the protein under consideration, rather than the response to perturbing forces that may be much larger than the stabilizing forces inherent in the protein. In the FIG. 3 example, the target collective coordinate $Q_c$ 102 is decreased over a series of time steps until a final target value 104 that may typically range from 0.4 to 0.8. In some embodiments, this final target $Q_c$ value 104 is in a range of 0.5 to 0.7.

There is some freedom in setting the value of the constant k in equation (3). In some embodiments, this value k may be set in a range of $2\times10^4$-$1\times10^5$ kJ/mol, depending on the rate at which the target collective coordinate $Q_c$ is changing. In some embodiments, this value k may be set in a range of $4\times10^4$-$8\times10^4$ kJ/mol. In one exemplary embodiment, k is set to be k=$6\times10^4$ kJ/mol, which provides small deviation of the actual collective coordinate Q 34 from the target collective coordinate $Q_c$ 102 (yielding a value of Q–$Q_c$ of approximately 0.02), when $Q_c$ was changing at a rate of about 0.4 per 15 nanoseconds (see FIG. 3). The slower the biasing rate (i.e. the slower the rate of change of the target collective coordinate 100), the smaller the value of k that is acceptable. The value of k may be chosen to provide a small number for the deviation Q–$Q_c$, such as Q–$Q_c$ of approximately 0.02, by applying a suitable energetic cost when the system deviates from the target $Q_c(t)$. If the constant k is too small, Q will tend to deviate too largely from $Q_c$; on the other hand, if k is too large, the system will be energetically unstable due to large artificial forces induced by even small deviations from the minimum of the potential V(Q,t) in equation (3).

For a given protein under consideration, some embodiments involve performing the method 10 simulation a number of times (or at least loop 25 a number of times), where each biasing simulation is independent. This is illustrated in FIG. 1 by block 45 which involves an inquiry as to whether or not to perform another independent run. If the block 45 inquiry is positive, then method 10 loops back to perform simulation loop 25 again. In the illustrated embodiment, method 10 loops back to block 20, but this is not always necessary. In some embodiments, method 100 may loop back to other functional blocks. As described in more detail below number of independent biasing simulations (which may be referred to as runs) may help to ensure that polymer regions that are observed to be exposed (i.e. unfolded) in any given simulation are indeed consistently exposed over a plurality of simulations, and not the result of a rare random fluctuation in a particular stochastic molecular dynamics simulation. Some embodiments thus consider regions of a protein (to be potential candidate epitope predictions 52) for which at least a significant fraction f over the number of independent simulations showed one or more indicia of unfolding (e.g. increase in exposure) of the region upon biasing.

In some embodiments, the fraction f is selected to be greater than 0.8. In some embodiments, the fraction f is selected to be greater than 0.85. In one particular example embodiments, the fraction f is selected to be f=0.87, which would correspond to either 7 of 8 simulations displaying an epitope, 8 of 9 simulations displaying an epitope, or 9 of 10 simulations displaying an epitope, and so on. The number of independent simulations may typically be greater than or equal to 8, although this is not necessary.

When the protein under consideration comprises an aggregated fibril structure, such as the Aβ fibrils described below, a region may be considered to be an epitope if, in a given simulation, the region exhibits one or more indicia of unfolding (e.g. is exposed) in any of the monomers (any of the peptide chains), and that such an epitope is found to be exposed reliably in a fraction g of the simulations. In some embodiments, the fraction g is selected to be greater than 0.8. In some embodiments, the fraction g is selected to be greater than 0.85. In one particular example embodiments, the fraction g is selected to be g=0.87.

If the block 45 inquiry is negative, method 10 proceeds to block 50. Block 50 comprises analyzing the simulation results of the block 25 simulations (e.g. each iteration or run through simulation loop 25) in effort to identify candidate epitopes. In the FIG. 1 embodiment, block 50 is depicted as being performed output of the block 25 simulation loop. This is not necessary. In some embodiments, some or all of block 50 may be performed within simulation loop 25.

Figure 4A:
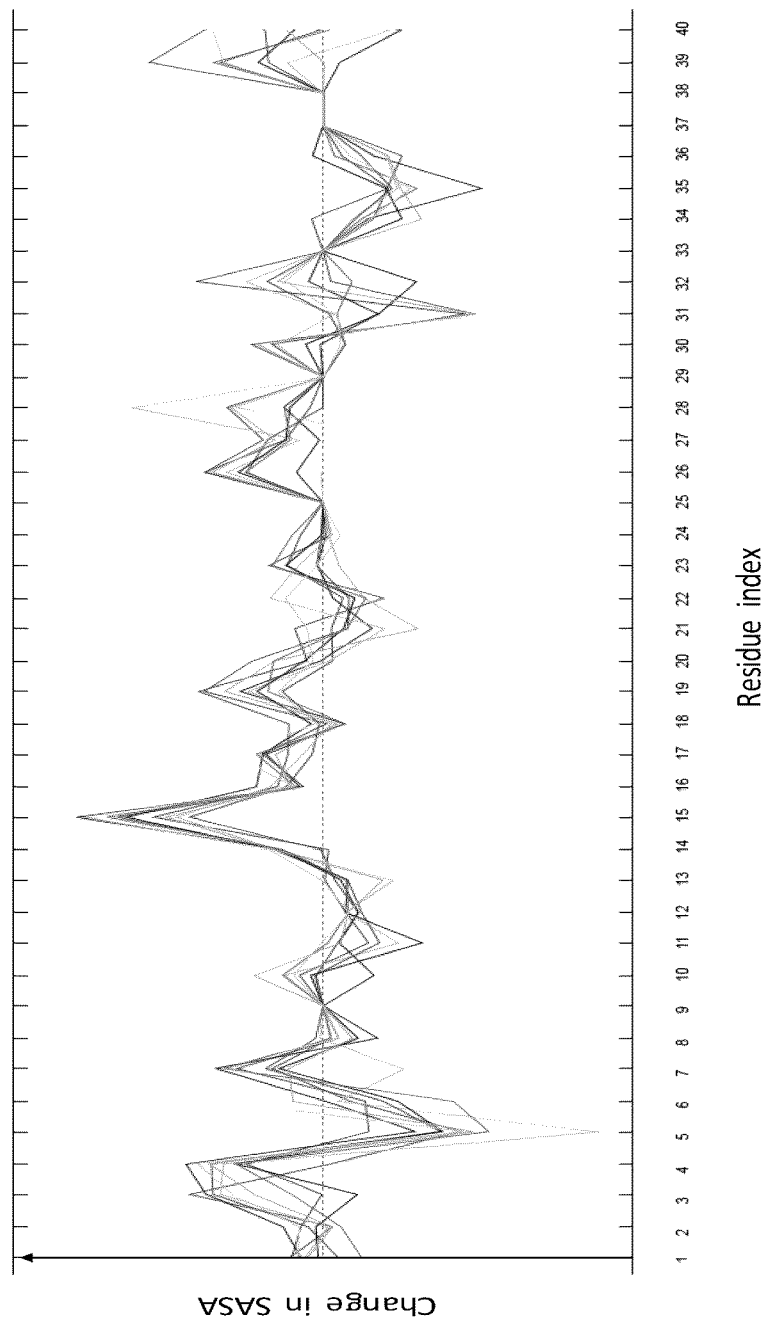
FIG. 4A shows a plot of the change in solvent-accessible surface area (SASA) of the side chains of amino acids, as compared to the SASA of their initial structure as a function of residue index for each residue in the sequence, for one monomer of the 3-fold symmetric Aβ structure 2M4J, when biased to 80% of its initial structure. Each curve in the plot corresponds to a separate biasing simulation for this monomer.
Figure 4B:
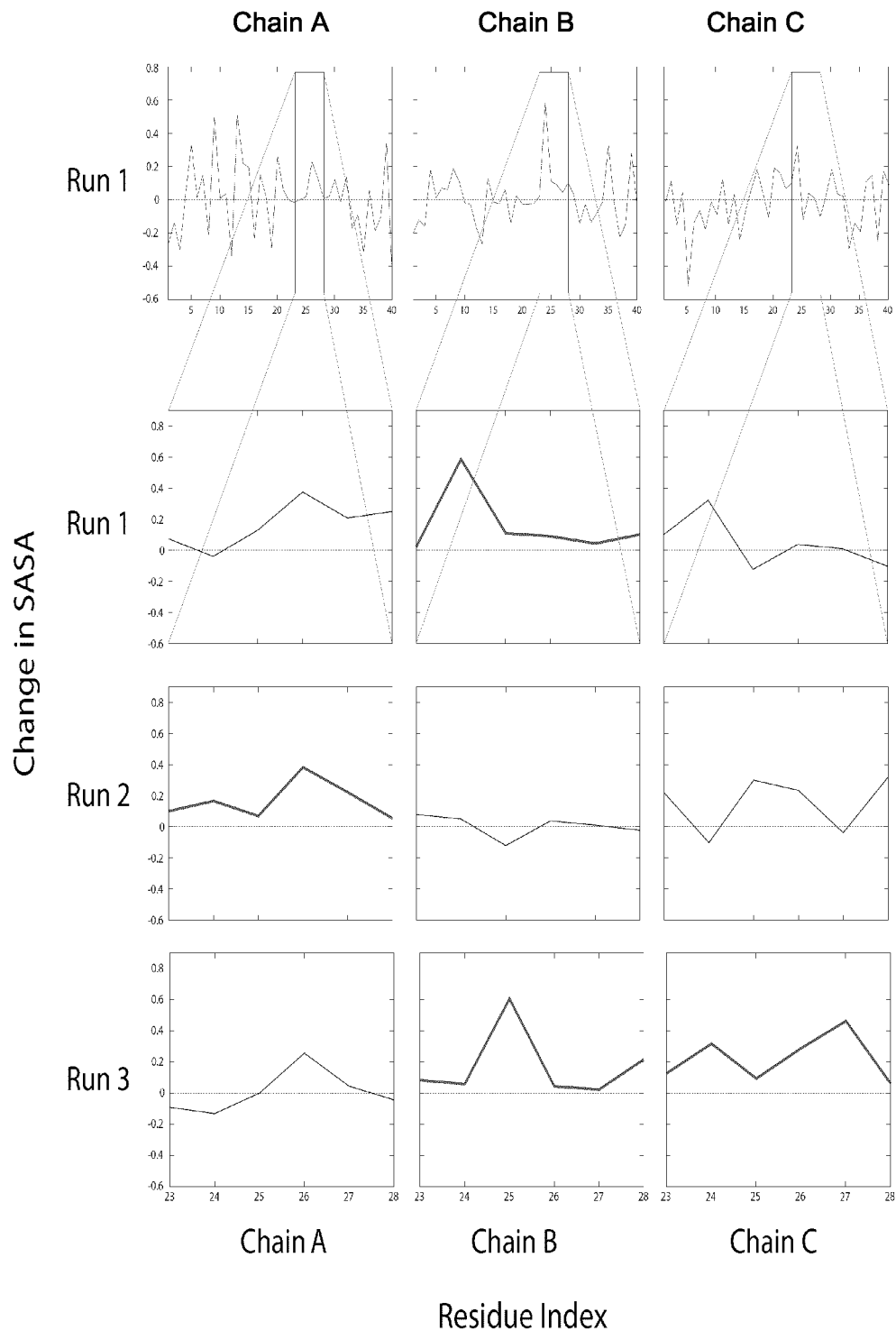
FIG. 4B schematically depicts the analysis of the FIG. 1 method for an exemplary aggregated structure where a given segment (e.g. residues 23 to 28) for each chain is considered independently and each simulation run is considered independently.

FIGS. 4A and 4B depict exemplary simulation result data for an exemplary aggregated structure that may be subjected to method 100. In particular, FIG. 4A shows a change in solvent accessible surface area (SASA) upon biasing to a target collective coordinate $Q_c$ which is 0.8 of the initial Q versus residue index for chain B of the three-fold symmetric Aβ structure 2M4J and FIG. 4B schematically depicts the application of the FIG. 4 method to an exemplary aggregated structure where a given segment (e.g. residues 23 to 28) for each chain is considered independently and each simulation run is considered independently. The FIG. 4B data is simulation data from Aβ40, with only three peptide chains and three simulations shown purely for illustrative clarity. In the particular case of the method illustrated in FIGS. 4A, 4B, 5A, 5B and 5C, the data used for the block 50 candidate epitope selection process is obtained, for each run of simulation loop 25, a suitable time after the collective coordinate bias has reached its final level, which allows the system under consideration to come to an equilibrium. In the particular case of the collective coordinate bias described by equations (1)-(3), the data used for the block 50 candidate epitope selection process may be obtained a suitable time (e.g. on the order of 20-200 ns) after $Q_c$ has reached its final level (see FIG. 3).

FIG. 4A shows an illustrative example plot of the change in solvent-accessible surface area (SASA) for each residue as a function of residue index, for one peptide chain of the 3-fold symmetric Aβ structure 2M4J, after biasing to 80% of its initial structure, for 10 independent simulations. Each FIG. 4A trace shows the result from one simulation (or run). The X-axis of the FIG. 4A plot is the amino acid (or residue) index for the illustrated peptide chain. SASA represents a surface area that is accessible to $H_2O$. The Y-axis of the FIG. 4A plot is the change in SASA (ΔSASA) for the updated structure 32 (FIG. 1) at the conclusion of each of the independent simulations (compared to that of the initial structure 22 of the protein under consideration). A positive ΔSASA may be considered to be indicative of unfolding in the region of the associated residue index. This ΔSASA parameter is a non-limiting example of a local unfolding indicia 54 which may be generated in block 50 based, at least in part, on the updated structure models 32 determined in simulation loop 25 and/or comparisons of the updated structure models 32 to the initial structure model 22 (see FIG. 1) and which may be determined on a local (e.g. per residue) basis. In some embodiments, additional or alternative local unfolding indicia 54 may be determined and/or analyzed in block 50 on a local (e.g. per residue basis) to assist with the prediction of candidate epitopes 52. Such local unfolding indicia 54 may be based on the updated structure models 32 determined in simulation loop 25 and/or comparisons of the updated structure models 32 to the initial structure model 22. By way of non-limiting example, such additional or alternative local unfolding indicia 54 may include: a number of lost contacts (when comparing the updated structure model 32 to the initial structure model 22) for each residue, the root mean squared fluctuations (RMSF) of an updated structure model 32 relative to a native structure model 22 for each residue, which is representative of how much motion a residue undertakes in a given ensemble of conformations, a number of lost backbone hydrogen bonds (when comparing the updated structure model 32 to the initial structure model 22) for each residue, the potential energy of interaction for each residue (when comparing the updated structure model 32 to the initial structure model 22), combinations of the above parameters, and/or the like.

For the FIG. 4A example at a collective coordinate biasing of 80% the initial structure (e.g. $Q_c=0.8Q_{initial}$), we see two regions emerging with reliably increased SASA: residues 14-17 and residues 25-30. In the embodiment shown in FIG. 4A, only the change in side-chain surface exposure is shown, so that all glycine residues necessarily have a change in SASA of zero, but do not penalize the prediction. Other embodiments count the change in SASA of the backbone of glycine residues. For some embodiments including the illustrative example embodiment of method 100 (FIG. 4), the block 50 analysis searches for regions in which a suitable threshold fraction f of the ten independent runs show an increase in exposure (e.g. a ΔSASA>0)—in this plot those regions are residues 14 to 17 and 25 to 30.

FIG. 4B shows illustrative example results for an example aggregate structure (here taken from PDB 2M4J) of three identical peptide chains (Chain A, Chain B, and Chain C as indicated by the columns in FIG. 4B; each peptide chain—hereafter referred to as a "chain"—may be a copy Aβ peptide in a fibril, for example) wherein biasing simulations have been replicated three times (Run1, Run2, and Run3 as indicated by the rows in FIG. 4B). Each column in FIG. 4B indicates the same peptide chain, but in different simulation runs, while each row indicates the same simulation run, but different peptide chains. The bottom 3×3 array of plots in FIG. 4B is a "zoom-in" on a particular group of residuers consisting of residues 23-28. The full range of residues is indicated in the top row of FIG. 4B, for simulation run 1. The X-axis of each FIG. 4B plot comprises a residue index (e.g. an amino acid index). The Y-axis of each FIG. 4B plot represents the change in solvent accessible surface area (ΔSASA) corresponding to each residue index (compared to that of the initial structure of the chain under consideration). For each of the three chains across the horizontal axis of FIG. 4B, the top plot shows the ΔSASA for a range of residue indices from 1 to 40 for first independent simulation ("run 1"), the second plot from the top shows detail of the ΔSASA for indices 23-28 in run 1, the third plot from the top shows detail of the ΔSASA for indices 23-28 in a second simulation ("run 2") and the bottom plot shows detail of the ΔSASA for indices 23-28 in a third simulation ("run 3").

For a given chain segment (here residues 23 to 28), each chain (i.e. each column of FIG. 4B) is analyzed independently. In the illustrated embodiment, an epitope may identified if, for each run (i.e. each of rows 2, 3 and 4 of FIG. 4B), there is at least one chain in which all the residues of the peptide sequence of interest have a positive ΔSASA upon biasing. In the FIG. 4B illustration, the chain segments satisfying this criterion for a given run are shown in bold (middle panel of run 1 row, left panel of run 2 row, and middle and right panels of the run 3 row), while those not satisfying the criterion are in thinner lines. The data in FIG. 4B is simulation data from Aβ-40 starting from PDB structure 2M4J, with only three chains and three simulations shown for clarity. The FIG. 4B example shows how the group of epitopes would be selected, either as a potential candidate epitope or as part of a larger potential candidate epitope, because it is exposed in at least one chain in every simulation run or, more generally, in greater than or equal to a suitable threshold fraction f of the number of simulation runs.

As discussed above, ΔSASA for a given simulation represents only one local unfolding indicia 54 (FIG. 1) which may be used to identify epitopes in accordance with the simulation methods described herein. In some embodiments, other additional or alternative local unfolding indicia 54 that may be used to identify epitopes include, without limitation, a number of lost contacts (when comparing the updated structure model 32 to the initial structure model 22) for each residue, the root mean squared fluctuations (RMSF) of an updated structure model 32 relative to a native structure model 22 for each residue, which is representative of how much motion a residue undertakes in a given ensemble of conformations, a number of lost backbone hydrogen bonds (when comparing the updated structure model 32 to the initial structure model 22) for each residue, the potential energy of interaction for each residue (when comparing the updated structure model 32 to the initial structure model 22) for each residue, combinations of the above parameters, and/or the like. Such local unfolding indicia 54 may be based on the updated structure models 32 determined in simulation loop 25 and/or comparisons of the updated structure models 32 to the initial structure model 22. To reduce susceptibility to stochastic thermal fluctuations, local unfolding indicia 54 may be averaged over a plurality of time steps after the target collective coordinate has reached its final value. Since such averaging of local unfolding indicia 54 occurs after the target collective coordinate has reached its final value, such averaging of local unfolding indicia 54 may be referred to as equilibrium averaging. Unless the context dictates otherwise, references to local unfolding indicia 54 herein should be understood to include the possibility that local unfolding indicia 54 is equilibrium averaged.

As mentioned above, Aβ peptide tends to aggregate in several different polymorphic forms. Polymorphism exists for both the fibril form and the ensemble of oligomeric structures.

A number of the example results described herein represent results for a number of A fibril strains, each with its own morphology: a three-fold symmetric structure of 9 Aβ-40 peptides (or monomers) (PDB entry 2M4J), a two-fold symmetric structure of 12 A-40 monomers (PDB entry 2LMN), a single-chain, parallel in-register structure of 12 Aβ-42 monomers (PDB entry 2MXU; disordered N-terminal residues 1-10 have been added to this structural model), and a three-fold symmetric structure of 18 Aβ-40 monomers (PDB entry 2LMP; disordered N-terminal residues 1-8 have been added to this structural model). Two additional computational assays were performed, one on structure 2LMN by adding disordered residues 1-8 at the N-terminus (these are missing from the PDB structure), and one assay on structure 2MXU by constraining the top and bottom monomers along the fibril to remain in their structured conformation, and allowing the middle 10 monomers to disorder. Simulations were performed for each initial structure (using loop 25 of method 10 and the CHARMM force-field parameters described in: K. Vanommeslaeghe, E. Hatcher, C. Acharya, S. Kundu, S. Zhong, J. Shim, E. Darian, O. Guvench, P. Lopes, I. Vorobyov, and A. D. Mackerell. Charmm general force field: A force field for drug-like molecules compatible with the charmm all-atom additive biological force fields. *Journal of Computational Chemistry,* 31(4):671-690, 2010; and P. Bjelkmar, P. Larsson, M. A. Cuendet, B. Hess, and E. Lindahl. Implementation of the CHARMM force field in GROMACS: analysis of protein stability effects from correlation maps, virtual interaction sites, and water models. *J. Chem. Theo. Comp.,* 6:459-466, 2010, both of which are hereby incorporated herein by reference, with TIP3P water. The simulations included a concentration of 0.1 M NaCl. Each system was equilibrated for 5 ns, during which time Q was measured to provide an initial value of $Q_c(t=0)$.

Unless otherwise indicated, the center of the biasing potential was moved to 0.6 of its original value over a time period of 15 ns, during which time the amount of structure initially present reduced systematically as described above, to about 60% of the original value. For one set of initial epitope predictions, the inventor analyzed structures corresponding to about 71% of the initial structure Q(t=0)—e.g. a collective coordinate Q corresponding to about 0.71 of the initial collective coordinate. As discussed above, the proteins under consideration were constrained to have 71% of the initial structure for a time window of typically about 100 ns.

For each protein under consideration, 9 or 10 (or some other suitable number) of independent runs may be performed with each independent run comprising random seeding of the thermostat random number generator of the molecular dynamics engine. Performing 9 or 10 (or some other suitable number) of independent runs gives some assurance that any predicted epitopes are genuine and not a rare or random occurrence. As discussed above, some embodiments comprise identifying an epitope as a potential candidate epitope if any chain exposes the epitope in a fraction f (e.g. f>0.87) of all the runs. After biasing and simulating the evolution of the protein under consideration (block 30), some embodiments comprise analyzing the results by ascertaining the extent to which each residue has unfolded by comparing the change in SASA (or other suitable measure of unfolding as discussed herein), from the initial structure to the structures in the ensemble after biasing. In embodiments which use SASA, some such embodiments may use the side chain surface area for every residue except glycine residues—for glycine, some embodiments may use the total residue surface area (which amounts to the backbone surface area for glycine).

One difference between the Aβ structures contained in the protein databank (PDB) (http://www.rcsb.org) and the empirical systems that the inventor has examined is that the PDB structures do not necessarily comprise all the residues of the chain; this is because some residues are disordered in the empirically determined system and so reliable coordinates cannot be deposited as part of the PDB structure. The structures corresponding to PDB ID 2LMN and PDB ID 2LMP contain only residues 9-40 for each monomer and are missing the N-terminal region consisting of residues 1-8, and the structure corresponding to PDB 2MXU contains only residues 11-42 for each monomer and is missing N-terminal residues 1-10. PDB 2M4J contains all 40 residues for each monomer. For PDB structures with missing N-terminal regions, some embodiments may comprise making final epitope predictions from systems where the disordered N-terminal region is explicitly added in to the PDB structures. The presence of a disordered N-terminal tail can be a potentially important effect because there is a polymeric entropy cost to tether a disordered terminal region to the rest of the structure, due to the steric non-crossing entropy of the polymer with the rest of the ordered protein or fibril. For this reason the predictions, specifically for N-terminal regions of 2LMN using the model with the N-terminus absent, are likely somewhat overemphasized.

FIGS. 5A, 5B and 5C schematically depict a method 100 for analyzing simulation results to identify epitopes in proteins which may be used as a part of block 50 in some embodiments. FIGS. 5A, 5B and 5C show a particular example of a method 100 which may be used as a part of block 50 for the case where the protein under consideration is an aggregate structure comprising a plurality of peptide chains.

FIG. 5A depicts a portion 102 of method 100 which is a generalization of the above discussed procedures described in connection with FIG. 4B. Portion 102 of method 100 may be referred to as method 102 for the sake of brevity. The procedures of the FIG. 5A method 102 may be performed once for each independent simulation (i.e. each run) and once for each peptide within each run. It will be appreciated that where the protein under consideration comprises a single chain, then method 102 may be performed once for each independent run. In the illustrated embodiment, method 102 describes how to get from the updated structure models 32 determined in simulation loop 25 (FIG. 1) to the type of matrix shown in the bottom nine plots of FIG. 4B. It will be appreciated that FIG. 4B shows a matrix of ΔSASA plots for a particular group of residues (residues 23-28 in the FIG. 4B example) and that the FIG. 4B matrix spans a number of independent runs and a number of chains in an aggregate structure. Similarly, method 102 shown in FIG. 5A may result in the generation of a matrix for each group from among a plurality of groups of residues. In general, these groups may have different sizes (which may be referred to as window sizes).

Method 102 commences in block 105 which involves determining local unfolding indicia 54 for each residue in the current run and current chain. As discussed above, local unfolding indicia may be determined on the basis of updated structural models 32 determined in the block 25 simulation loop. In the particular case of method 102 of the FIG. 5A embodiment, the local unfolding indicia that is used is ΔSASA, without loss of generality. Method 102 then proceeds to block 110 which involves initializing a window size parameter. In subsequent iterations, block 110 may comprise incrementing the window size parameter. The block 110 window size parameter represents the size of the group (i.e. the number of residues) considered to determine whether there is a positive ΔSASA in a particular iteration of method 102. In the case of the FIG. 4B example, the residues under consideration were residues 23-28, corresponding to a window size of 6. As will be explained in more detail below, each window size may represent a row of the fireplot matrices shown in FIG. 6.

Method 102 then proceeds to block 120 where the residue index of the current peptide chain is parsed into a number of groups with each group having a number of residues equal to the current window size. It will be appreciated that for a given chain (having a given residue index), where the block 110 window size is larger, the number of block 120 groups will be lower and vice versa. Method 102 then proceeds to block 130 which initializes (first iteration) or increments (subsequent iterations) a group index counter. The group index counter may also be referred to as a window position or window position index.

Method 102 then proceeds to block 140 which involves an inquiry into whether the current group has a ΔSASA>0 for all residues in the group. If the block 140 inquiry is positive, method 102 proceeds to block 150, where a positive result is recorded for the current group, before ending up in block 170. In some embodiments, block 150 may comprise recording the ΔSASAs of the residues belonging to the current group and/or an accumulated sum of the ΔSASAs of the residues belonging to the current group, although this is not necessary, since this information is available from block 105. If the block 140 inquiry is negative, method 102 proceeds to block 160, where a negative results is recorded for the current group, before ending up in block 170. Block 170 involves an inquiry into whether the current group is the last group in the current chain. If the current group is not the last group, then method 102 loops back to block 130, where the group index is incremented for another iteration. If the block 170 inquiry is positive, then method 102 proceeds to block 180 which involves an inquiry into whether the current window size is the maximum window size to be considered. In some embodiments, the maximum window size is set to 12 residues. In some embodiments, this maximum window size may be 10 residues. If the current window size is not the maximum window size, then method 102 loops back to block 110, where the window size is incremented for another iteration.

If the current window size is the maximum window size, then method 102 concludes and moves on to method 202 of FIG. 5B described in more detail below. At the conclusion of method 102, method 100 has determined, for a particular chain and a particular run, a number of residue groups of various different sizes which exhibit a local unfolding indicia 54 that is indicative of unfolding for the groups (e.g. ΔSASA>0 for all of the residues in the groups, in the case of one particular embodiment). As discussed above, method 102 may be performed once for each chain of a protein under consideration and once for each simulation run for the protein under consideration to develop similar information for various residue groups over the various peptide chains and various independent simulation runs. It will be appreciated that after performing method 102 for each chain and each independent run, method 102 may generate a matrix of data similar to that illustrated in FIG. 4B for each of a plurality of residue groups (i.e. a matrix that spans a number of chains and a number of runs) for each of a plurality of residue groups and for which it may be capable of discerning whether the group exhibits indicia of localized unfolding.

Figure 5A:
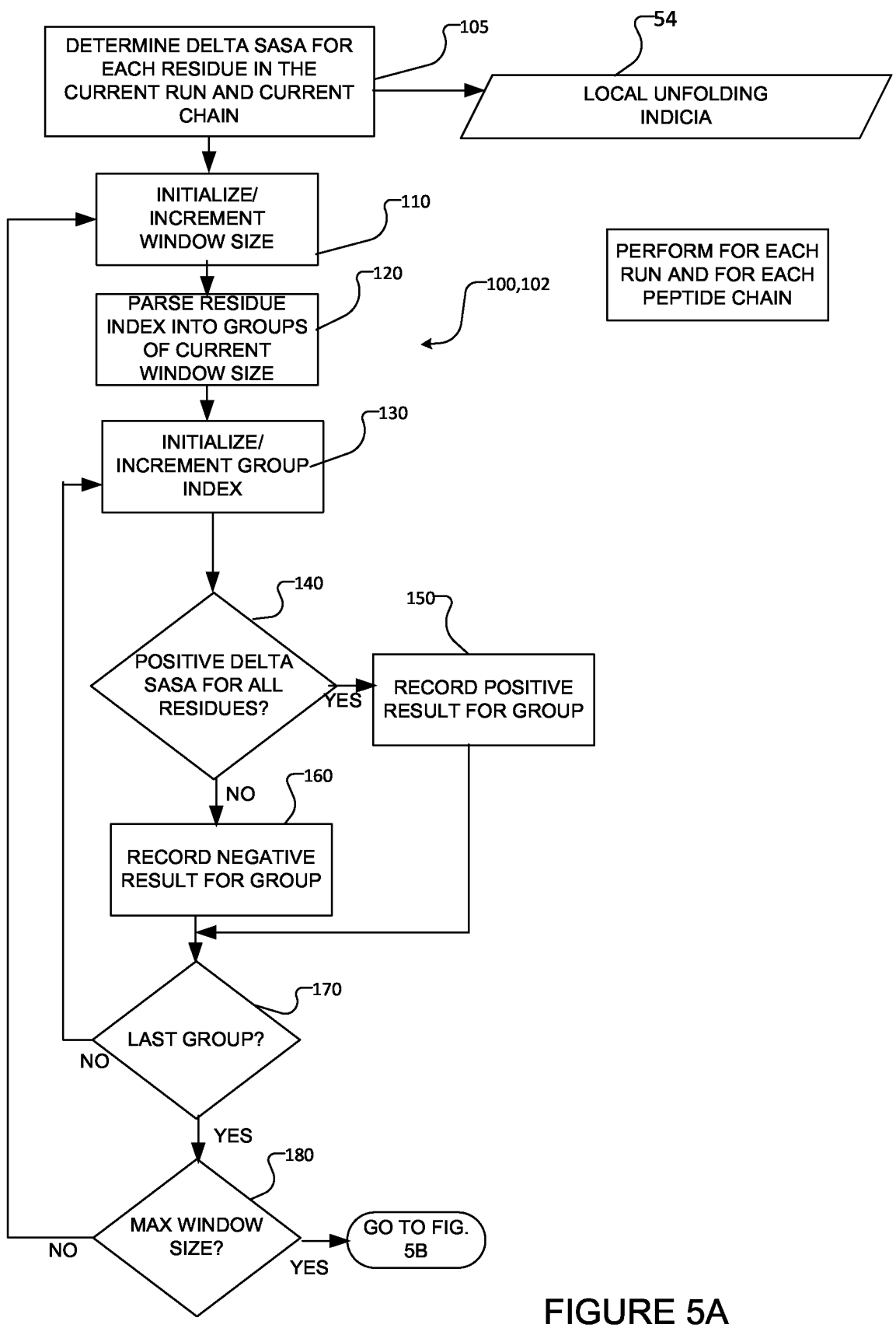
FIGS. 5A, 5B and 5C (collectively FIG. 5) schematically depict a method for analyzing simulation results to identify candidate epitopes in proteins comprising aggregated systems which may be used in the method of FIG. 1 or which may be otherwise used in a candidate epitope prediction method according to a particular embodiment.
Figure 5B:
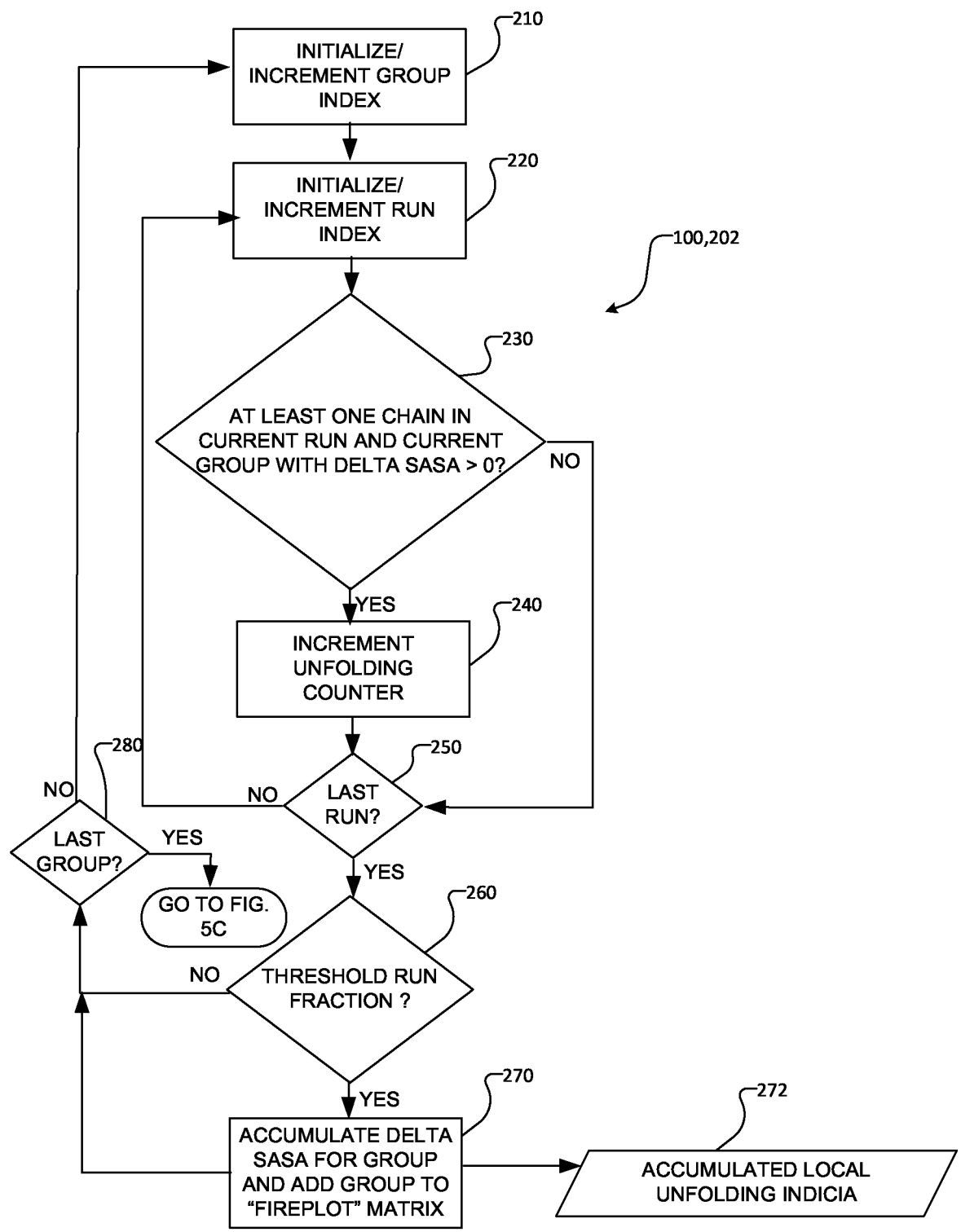

At the conclusion of the execution of method 102 for each run and for each peptide chain, method 100 may proceed to portion 202 of method 100 shown in FIG. 5B. Portion 202 of method 100 may be referred to as method 202 for brevity. As discussed above, some embodiments may consider a group of residues of a protein (to be potential candidate epitope predictions 52) where at least a significant fraction f over the number of independent simulations showed one or more indicia of unfolding (e.g. increase in exposure) of the group upon biasing. As discussed above, where the protein under consideration is an aggregate structure, a group of residues may be considered to be a potential candidate epitope if, in a given simulation, the group of residues exhibits one or more indicia of unfolding (e.g. is exposed) in any of the monomers (any of the peptide chains), and that such an epitope is found to be exposed reliably in a fraction g of the simulations. In the example residue group shown in FIG. 4B, this exhibited indicia of unfolding in any of the peptide chains over a fraction g of the total number of independent runs was described as requiring that at least one of the FIG. 4B chains (A, B and C) exhibited ΔSASA greater than zero for the group under consideration in at least a fraction g of the total number of independent runs. In the illustrated embodiment, method 202 describes this thresholding process and how to get to the type of data which illustrated in the "fireplots" of FIG. 6.

Method 202 commences in block 210 which comprises initializing (in the first iteration) and incrementing (in other iterations) a group index. The block 210 group index may refer to one of the residue groups for which data is obtained in method 102. Method 202 then proceeds to block 220 which involves initializing (in a first iteration) and incrementing (in subsequent iterations) a run index. The block 220 run index may refer to a particular one of the independent runs. Method 202 then proceeds to block 230 which involves an inquiry into whether there is at least one chain, for the current run and the current group, which has a ΔSASA>0 for all of the residues in the current group. This block 230 inquiry is equivalent to inquiring as to whether there is at least one chain, for the current run and the current group, which has a positive result recorded in block 150 (FIG. 5A). Where the protein being considered is not an aggregate structure, then the block 230 inquiry may consider whether the protein under consideration, for the current run and the current group, has a ΔSASA>0 for all of the residues in the current group. If the block 230 inquiry is positive, then method 202 moves to block 240 which comprises incrementing an unfolding counter before ending up in block 250. If the block 230 inquiry is negative, then method 202 moves directly to block 250 without incrementing the unfolding counter.

Block 250 involves an inquiry into whether the current run is the last run. If not, then method 202 loops back to bock 220 where the run index is incremented prior to another iteration. If the block 250 inquiry is positive, then method 202 proceeds to block 260 which involves an inquiry into whether the current residue group is indicated to be a potential candidate epitope in a sufficient fraction f, g of the independent runs. This fraction f, g, may a configurable parameter. As discussed elsewhere herein, some embodiments may consider a group of residues of a protein (to be potential candidate epitope predictions 52) where at least a significant fraction f over the number of independent simulations showed one or more indicia of unfolding of the group upon biasing (e.g. a ΔSASA>0 for all of the residues in the group). As discussed above, where the protein under consideration is an aggregate structure, a group of residues may be considered to be a potential candidate epitope if, in a given simulation, the group of residues exhibits one or more indicia of unfolding in any of the peptide chains (e.g. a ΔSASA>0 for all of the residues in the group), and that such an epitope is found to be exposed reliably in a fraction g of the simulations. If the block 260 inquiry is negative, then method 202 proceeds to block 280 which involves an inquiry into whether the current group is the last group. If the block 280 inquiry is also negative, then method 202 loops back to block 210, where the group index is incremented prior to another iteration of method 202. If the block 260 inquiry is positive, then the current group may be considered to be a potential candidate epitope and method 202 proceeds to block 270.

Block 270 involves generating a data structure comprising data (accumulated local unfolding indicia 272) of the type which is shown In the FIG. 6 "fireplots". For a particular group (i.e. the current group in method 202) block 270 may comprise accumulating a combined local unfolding indicia 272 for all instances of that group where each of the residues in the group exhibit a local unfolding indicia 54 indicative of localized unfolding. For example, where local unfolding indicia 54 is ΔSASA, block 270 may comprise (for the current group in method 202) accumulating a combined local unfolding indicia 272 which comprises a combined (e.g. added or averaged) ΔSASA for all instances of that group where each of the residues in the group exhibit ΔSASA>0. The accumulated or combined local unfolding indicia 272 (indexed by group) is the type of data that is used to provide the data structure shown in the FIG. 6 fireplots and explained in more detail below. For a particular group, the block 270 data generated may comprise the accumulated local unfolding indicia 272, together with a group length or window size (i.e. the number of residues in the group) and a group residue reference. In some embodiments, the group residue reference may comprise the middle residue of the group. In some embodiments, a custom is adopted where, if the number of residues in the group is even, the residue having an index just below the middle of the group is selected to be the group residue reference. In some embodiments, a different custom could be adopted for assigning the group residue reference. For example, the a custom could be adopted where the residue with the lowest index in a group could be selected as the group residue reference.

Eventually, method 202 proceeds to block 280 (either via the block 260 NO branch or via block 270). When the block 280 inquiry is positive, then method 202 is completed.

As discussed above, the data structures generated by method 202 may be represented in the form of fireplots, such as the exemplary fireplots shown in FIG. 6. FIGS. 6A-6D show several "fireplots" giving epitope predictions for three exemplary fibril strains (PDB 2M4J, 2LMN and 2MXU) considered in this disclosure (FIGS. 6A-6C), along with a prediction for PDB structure 2MXU (FIG. 6D) wherein the two cap monomers on either end of the fibril are constrained to not unfold. This FIG. 6D constraint mimics the boundary conditions present for a long fibril. The X-axes of the FIG. 6 plots indicate the residue index of the group residue reference. As discussed above in relation to block 270 of method 202, in some embodiments a center residue of a corresponding group of residues is considered to be the group residue reference. Each rectangle shown in the FIG. 6 fireplots is a group residue reference that refers to a group of underlying residues. The Y-axes of the FIG. 6 plots indicate the sequence length of the corresponding group (i.e. the number of residues/window size of the group or potential candidate epitope). As indicated by the legends shown on the side of the FIG. 6 plots, the grey-scale shading in the FIG. 6 plots is indicative of the accumulated local unfolding indicia 272 for the identified groups. In the case of the illustrated FIG. 6 embodiment, this accumulated local unfolding indicia comprises a sum of the ΔSASA for the residues in each group. All of the FIG. 6 plots are shown for a collective coordinate target value of $Q_c$=0.71. Other values of $Q_c$ may be used for epitope predictions—they tend to give similar results (see, for example, FIG. 7, which shows "fireplots" at several values of Q. The bottom two panels show two different equilibration times at the same value of Q).

Figure 5C:
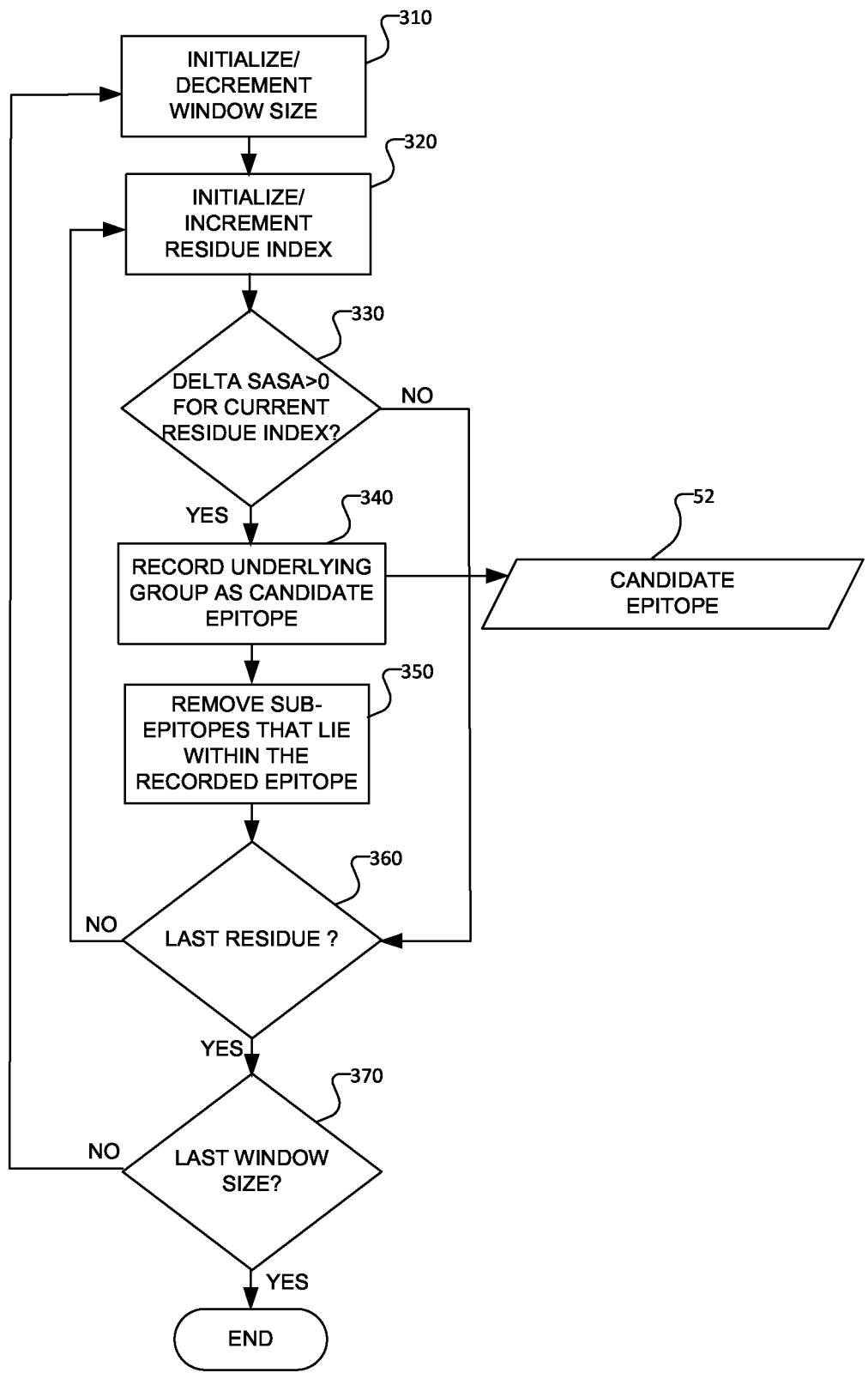
Figure 8:
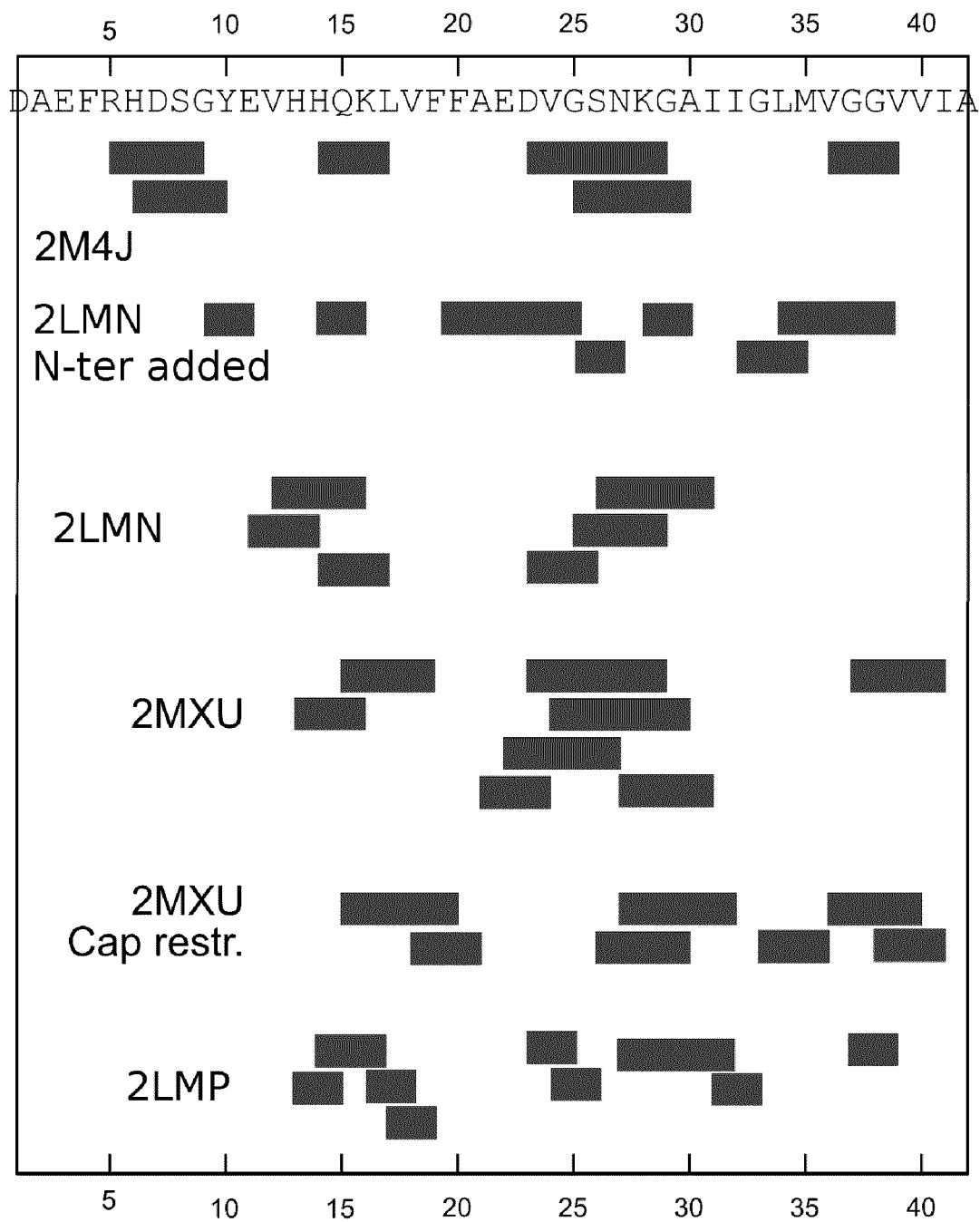
FIG. 8 shows a number of predicted epitopes for a number of proteins described herein.

At the conclusion of the execution of method 202 (FIG. 5B), method 100 may proceed to portion 302 of method 100 shown in FIG. 5C. Portion 302 of method 100 may be referred to as method 302 for brevity. Method 302 comprises using the data structures of the form represented by the FIG. 6 fireplots to predict the final candidate epitopes 52 (FIG. 1). For the case of the fireplots shown in FIG. 6, the final candidate epitopes 52 are shown in FIG. 8 and in Table 1 below.

Method 302 commences in block 310 which involves initializing a window size to be a maximum window size (in a first iteration) and then decrementing the window size in subsequent iterations. In some embodiments, the maximum window size is set at 12 residues in length, meaning that candidate epitopes predicted by method 302 will have a maximum possible length of 12 residues. In some embodiments, the maximum window size is set at 10 residues in length. If it is expected or discovered that a candidate epitope may be longer than 10 or 12 residues, then the maximum window size may be set to a larger number, as appropriate. Initializing the window size to be the maximum window size at the outset of method 302 effectively means that method 302 is starting its search at the top of the Y-axis of the FIG. 6 fireplots. After block 302, method 300 proceeds to block 320 which involves initializing (in a first iteration) and incrementing (in subsequent iterations) a residue index which will allow method 302 to scan across the group residue references (rectangles in the FIG. 6 fireplots) at a particular window size (i.e. across horizontal rows of the FIG. 6 fireplots) looking for hits, wherein a group residue reference has non-zero accumulated local unfolding indicia.

After initializing the residue index in block 320, method 302 proceeds to block 330 which involves an inquiry into whether the accumulated local unfolding indicia 272 is greater than zero for the current residue index and current window size. In particular embodiments where the local unfolding indicia 54 is ΔSASA, the block 330 inquiry may involve an inquiry into whether the accumulated ΔSASA is greater than zero for the current residue index and current window size. A positive block 330 inquiry corresponds to the existence of a rectangle in a particular row (window size) and column (residue index) of the FIG. 6 fireplots. If we consider the example case of the fireplot data structure shown in FIG. 6A, the first positive block 330 inquiry will occur for window size 7 and residue index 26—i.e. (residue index,size)=(26,7). For the custom (used in FIG. 6) where the group residue reference corresponds to the middle residue of the underlying group, the group (candidate epitope) associated with this positive block 330 inquiry comprises the residues 23-29.

If the block 330 inquiry is positive, then method 302 proceeds to block 340, where the group of residues underlying the block 330 "hit" is identified and recorded as a candidate epitope 52 predicted by method 10 (FIG. 1). For the example of FIG. 6A, this block 340 candidate epitope 52 (i.e. (residue index,size)=(26,7)) is shown in Table 1 (below) and as the longest candidate epitope shown in FIG. 8 for the structure 2M4J being considered in FIG. 6A.

Method 302 then proceeds to block 350 which involves removal, from further consideration, of the candidate epitope 52 recorded in block 340 and all sub-epitopes that lie within the candidate epitope 52 recorded in block 340. In the case of the illustrated FIG. 6A example, block 350 may comprise removing the candidate epitope 52 recorded in block 340 (i.e. the 7 residue epitope at (residue index, size)=(26,7)) from the FIG. 6A.

Figure 16:
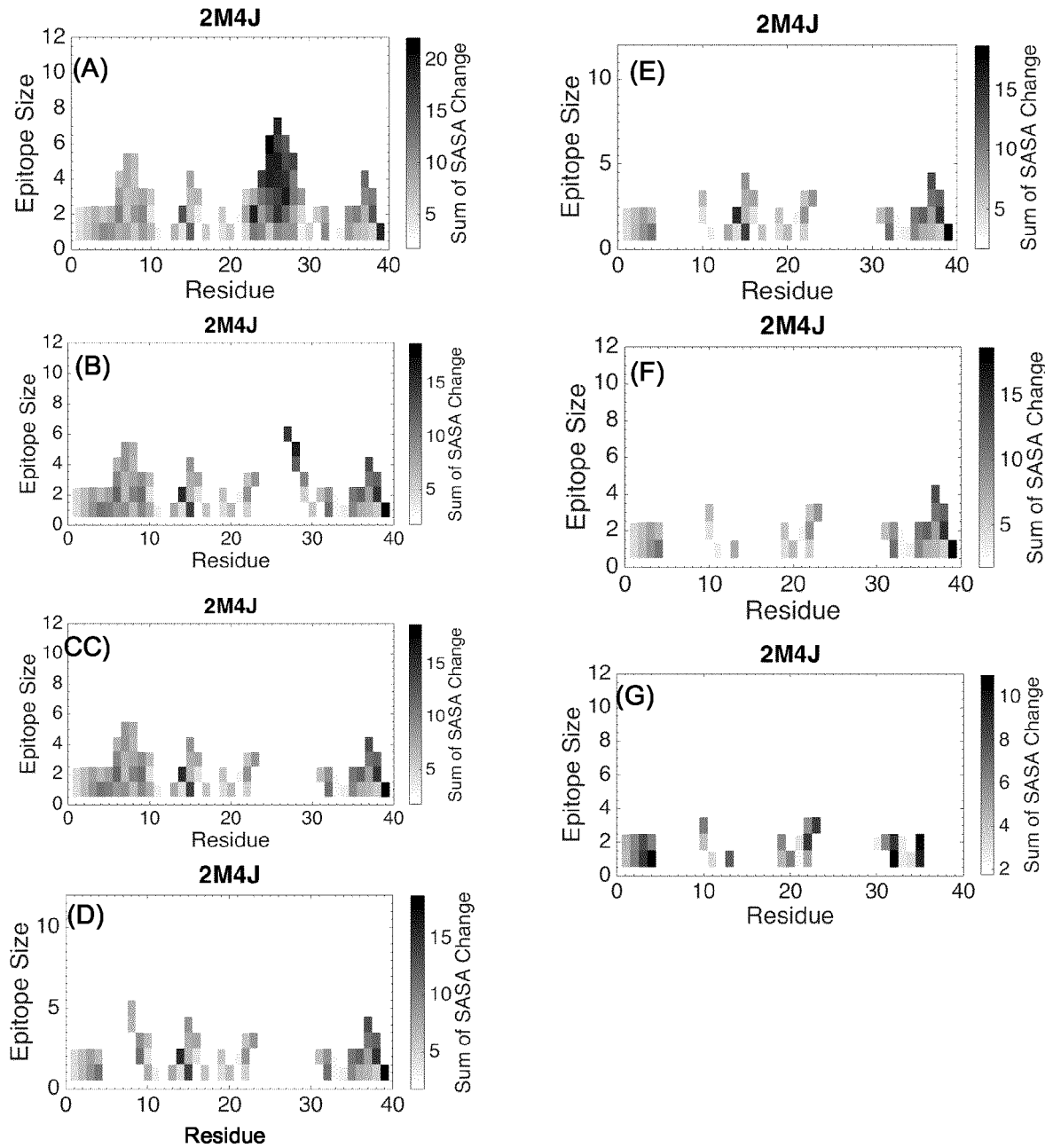

Block 350 also comprises removing the sub-epitopes that lie within the block 340 candidate epitope 52 In the case of the FIG. 6A fireplot, the first block 340 candidate epitope at (residue index,size)=(26,7) which includes residues 23, 24, 25, 26, 27, 28 and 29. Accordingly, sub-epitopes of (26,7) that would also be removed in block 350 include the rectangles at (25,6) and (26,6), which respectively correspond to residues 23, 24, 25, 26, 27, 28 and 24, 25, 26, 27, 28, 29 and which are within the first block 340 candidate epitope 52 at (residue index,size)=(26,7). Other sub-epitopes that are removed as part of block 350 for the FIG. 6A case where the first block 340 candidate epitope 52 is at (residue index,size)=(26,7) include (25,5), (26,5), (27,5), (24,4), (25, 4), (26,4), (27,4), (23,2), (24,2), (25,2), (26,2), (27,2), (28, 2), (23,1), (24,1), (25,1), (26,1), (27,1), (28,1) and (29,1). The block 350 removal of sub-epitopes for the first block 340 candidate epitope 52 for the FIG. 6A fireplot (i.e. candidate epitope (26,7) is shown in FIG. 16 by comparing the FIG. 16 plot (A) to the FIG. 16 plot (B). Comparing these two plots shows the removal of sub-epitopes from a cone-shaped region having a base length that is the same as the size of the block 340 candidate epitope 52 at (26,7).

After removal of the candidate epitope 52 and sub-epitopes in block 350, method 302 proceeds to block 360 which involves an inquiry as to whether the current residue index is the last residue index (e.g. the last residue in a row of the FIG. 6 fireplots). If the block 360 inquiry is negative, then method 302 loops back to block 320 where the residue index is incremented for another iteration. If the block 360 inquiry is positive, then method 302 proceeds to block 370 which involves an inquiry as to whether the window size is the last window size (e.g. the lowest row to be considered in the FIG. 6 fireplots). Typically, the smallest window to be considered in method 302 will be 3 or for residues in length. If the block 370 inquiry is negative, then method 302 loops back to block 310 where the window size is decremented for another iteration (i.e. a scan over a lower row of the FIG. 6 fireplots). If the block 370 inquiry is positive, then method 302 ends and the block 340 candidate epitopes 52 are output as the candidate epitopes 52 predicted by block 50 and method 10 of FIG. 1.

It will be appreciated by the above, that method 302 involves scanning row by row down from the top of the FIG. 6 fireplots looking for rectangles where the group residue reference indicates a non-zero accumulated local unfolding indicia 272. With the determination of each block 340 candidate epitope 52, the candidate epitope 52 and corresponding sub-epitopes are removed from further consideration. As discussed above, plot (B) of FIG. 16 shows the FIG. 6A fireplot after removal of the first candidate epitope 52 at (26,7) and its sub-epitopes. Method 302 continues to look in the fireplot (B) of FIG. 16 for additional candidate epitopes 52. The next candidate epitope 52 for which the block 330 inquiry is positive is at (residue index,size)=(27, 6)—see plot (B) of FIG. 16. This candidate epitope (corresponding to residues 25, 26, 27, 28, 29 and 30 according to the custom where, for a group of even residue length, the residue with an index just below the center is chosen as the group residue reference) is also shown in FIG. 8 and Table 1. The removal of this candidate epitope 52 and its sub-epitopes is shown in plot (C) of FIG. 16.

Method 302 continues scanning plot (C) of FIG. 16 for additional candidate epitopes. If several neighboring groups in the data underlying a FIG. 6 fireplot have the same length (e.g. the same y-axis height), each such group may be selected as a candidate epitope prediction 52. In the case of the FIG. 6A fireplot, two adjacent epitopes are present at (residue index,size)=(7,5) and (8,5) corresponding to residues 5-9 and 6-10. This implies that essentially the whole region defined by residues 5-10 may be a good candidate epitope 52. Further, in the case of FIG. 6A, two 4-residue length epitopes emerge, comprising residues 14-17, and 36-39. Epitopes for the other fibril strains may be constructed similarly from the data structures other FIG. 6 plots. FIG. 8 and Table 1 show the complete list of candidate epitopes 52 predicted by method 10 for the structures shown in the FIG. 6 fireplots. Predicted epitopes are sorted first by decreasing length, with the shortest prediction being 3 residues, then by residue index N-terminus to C-terminus.

Epitope predictions corresponding to the fireplots of FIGS. 6A-6D are made in Table 1, for each of the Aβ fibril morphologies—i.e. analysis of the fireplots in FIGS. 6A-6D using the methods described yields the epitopes listed in Table 1.

TABLE 1

| PROTEIN | PDB ID | PREDICTED EPITOPE RESIDUES | EPITOPE SEQUENCE |
|---|---|---|---|
| 3-fold Aβ40 | 2M4J | 23-29 | DVGSNKG (SEQ ID NO: 7) |
| | | 25-30 | GSNKGA (SEQ ID NO: 8) |
| | | 5-9 | RHDSG (SEQ ID NO: 9) |
| | | 6-10 | HDSGY (SEQ ID NO: 10) |
| | | 14-17 | HQKL (SEQ ID NO: 11) |
| | | 36-39 | VGGV (SEQ ID NO: 12) |
| 2-fold Aβ40 | 2LMN | 26-31 | SNKGAI (SEQ ID NO: 13) |
| | | 12-16 | VHHQK (SEQ ID NO: 14) |
| | | 25-29 | GSNKG (SEQ ID NO: 15) |
| | | 11-14 | EVHH (SEQ ID NO: 16) |
| | | 14-17 | HQKL (SEQ ID NO: 11) |
| | | 23-26 | DVGS (SEQ ID NO: 17) |

TABLE 1-continued

| PROTEIN | PDB ID | PREDICTED EPITOPE RESIDUES | EPITOPE SEQUENCE |
|---|---|---|---|
| Aβ42 | 2MXU | 23-29 | DVGSNKG (SEQ ID NO: 7) |
|  |  | 24-30 | VGSNKGA (SEQ ID NO: 18) |
|  |  | 22-27 | EDVGSN (SEQ ID NO: 19) |
|  |  | 15-19 | QKLVF (SEQ ID NO: 20) |
|  |  | 27-31 | NKGAI (SEQ ID NO: 21) |
|  |  | 37-41 | GGVVI (SEQ ID NO: 22) |
|  |  | 13-16 | HHQK (SEQ ID NO: 3) |
|  |  | 21-24 | AEDV (SEQ ID NO: 5) |
| Aβ42 Constrained Ends | 2MXU | 15-20 | QKLVFF (SEQ ID NO: 23) |
|  |  | 27-32 | NKGAII (SEQ ID NO: 24) |
|  |  | 26-30 | SNKGA (SEQ ID NO: 25) |
|  |  | 36-40 | VGGVV (SEQ ID NO: 26) |
|  |  | 18-21 | VFFA (SEQ ID NO: 27) |
|  |  | 33-36 | GLMV (SEQ ID NO: 28) |
|  |  | 38-41 | GVVI (SEQ ID NO: 29) |

Table 1: Predicted epitopes for the structures shown in FIGS. 6A-6D fireplots and corresponding to biases of Q = 0.71. They are ordered from longest epitope prediction to shortest, and then for epitopes of the same length, from N-terminus to C-terminus.

Table 2 shows predicted epitopes for a number of other structures considered by the inventor.

TABLE 2

| PROTEIN | PDB ID | PREDICTED EPITOPE RESIDUES | EPITOPE SEQUENCE |
|---|---|---|---|
| 2-fold Aβ40 N-term added | 2LMN | 19-25 | FFAEDVG (SEQ ID NO: 30) |
|  |  | 34-39 | LMVGGV (SEQ ID NO: 31) |
|  |  | 32-35 | IGLM (SEQ ID NO: 32) |
|  |  | 9-11 | GYE |
|  |  | 14-16 | HQK |
|  |  | 25-27 | GSN |
|  |  | 28-30 | KGA |
| 3-fold Aβ40 | 2LMP | 27-32 | NKGAII (SEQ ID NO: 24) |
|  |  | 14-17 | HQKL (SEQ ID NO: 11) |
|  |  | 13-15 | HHQ |
|  |  | 16-18 | KLV |
|  |  | 17-19 | LVF |
|  |  | 23-25 | DVG |
|  |  | 24-26 | VGS |
|  |  | 31-33 | IIG |
|  |  | 37-39 | GGV |

Table 2: predicted epitopes for a number of other structures considered by the inventor.

Figures 7A, 7B, 7C, 7D, 7E:
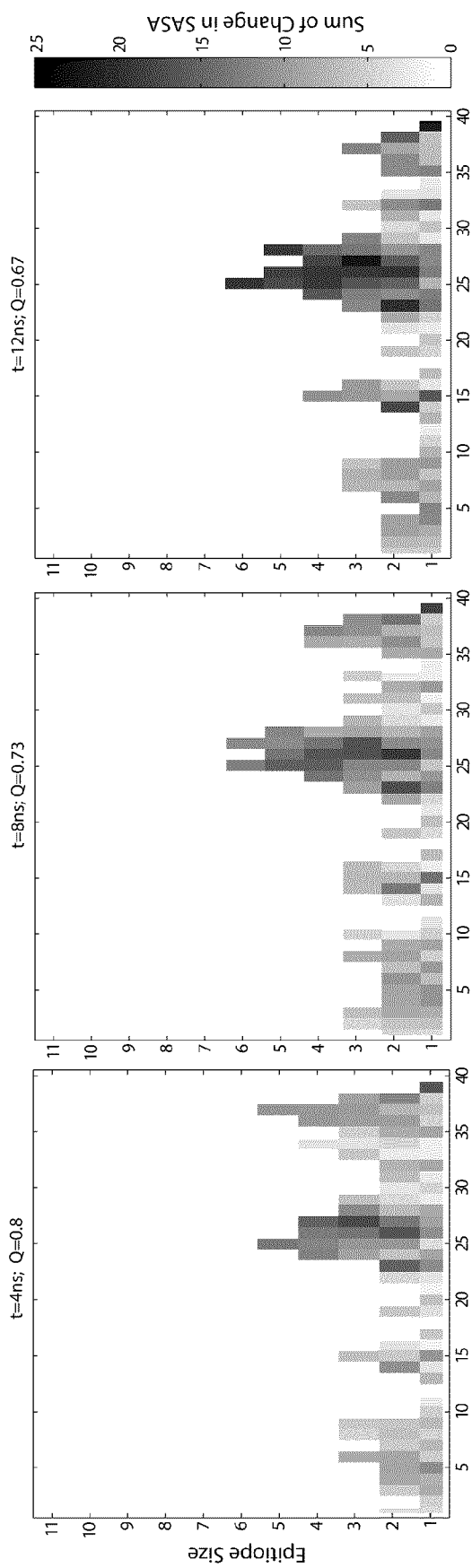

FIG. 7 shows fireplots similar to those of FIG. 6 for various levels of biasing (e.g. various final levels of the target collective coordinate), FIG. 7A shows Q=0.8, FIG. 7B shows Q=0.73, FIG. 7C shows Q=0.67, and FIG. 7D shows Q=0.6), with the particular final level of biasing (Q) shown above each plot. FIG. 7 demonstrates that the general structure of the predicted epitopes does not depend significantly on the degree of biasing. FIG. 7D and FIG. 7E show that final equilibration time does not have significant effects on the epitope prediction. For example, after 16 ns of equilibration (FIG. 7D), an epitope of length 4 centered at residue 8 is predicted (DSGY; SEQ ID NO: 33), while, after equilibrating for 20 ns (FIG. 7E), an epitope of length 5 centered at residue 8 is predicted (HDSGY; SEQ ID NO: 10). Thermal fluctuations may reduce or increase the size of epitope by the order of one residue at future times. Likewise, after 16 ns of equilibration (FIG. 7D), an epitope of length 7 centered at residue 26 is predicted (DVGSNKG; SEQ ID NO: 7), while, after equilibrating for 20 ns (FIG. 7E), two epitopes of length 6 are predicted, one centered at residue 25 (DVGSNK; SEQ ID NO: 34) and another centered at residue 27 (GSNKGA; SEQ ID NO: 8). The predictions at the two different equilibration times thus have strong overlap and are consistent with random thermal fluctuations.

The candidate epitopes 52 predicted by the methods described herein may be plotted for a variety of fibril models experimentally considered, and an emergent trend observed, see FIG. 8. Analysis of FIG. 8 yields several Aβ epitopes which have been previously experimentally supported. There is a strong persistent epitope predicted comprising approximately residues 25-30. This is consistent with a previous prediction for this region, see N. R. Cashman, *Oligomer-specific amyloid beta epitope and antibodies*, September 2011. Further validation of the candidate epitopes shown in FIG. 8 and in Tables 1 and 2 is described in U.S. patent applications No. 62/365,634 filed 22 Jul. 2016 and No. 62/393,615 filed 12 Sep. 2016.

For the single full-length structure considered herein, 2M4J, an N-terminal region emerges as an epitope prediction, roughly between residues 5-10. High-affinity polyclonal antibodies have been raised to the region consisting of residues 5-11, and these antibodies have also been observed to bind plaques and reduce neuritic pathology, see Frederique Bard, Robin Barbour, Catherine Cannon, Robert Carretto, Michael Fox, Dora Games, Teresa Guido, Kathleen Hoenow, Kang Hu, Kelly Johnson-Wood, Karen Khan, Dora Kholodenko, Celeste Lee, Mike Lee, Ruth Motter, Minh Nguyen, Amanda Reed, Dale Schenk, Pearl Tang, Nicki Vasquez, Peter Seubert, and Ted Yednock. Epitope and isotype specificities of antibodies to b-amyloid peptide for protection against Alzheimer's disease-like neuropathology. *Proc. Natl. Acad. Sci. USA*, 100(4):2023-2028, 2003.

A novel consensus-based epitope emerges from FIG. 8, appearing fairly consistently across strains, and consisting roughly of residues 13-18, or sequence HHQKLV (SEQ ID NO: 1). This epitope may be circularized to examine conformational selectivity for the oligomer. In addition to circularization to promote oligomer-specific selectivity, the epitope may also be transplanted into a protein scaffold to present the epitope in a specific conformation. The protein scaffold promotes conformational stabilization in the context of that protein structure. Such an epitope/scaffold may act as a structure-specific serological reagent, and/or as an immunogen to elicit antibodies with structural specificity to the epitope in the pathologic conformation.

Figure 9:
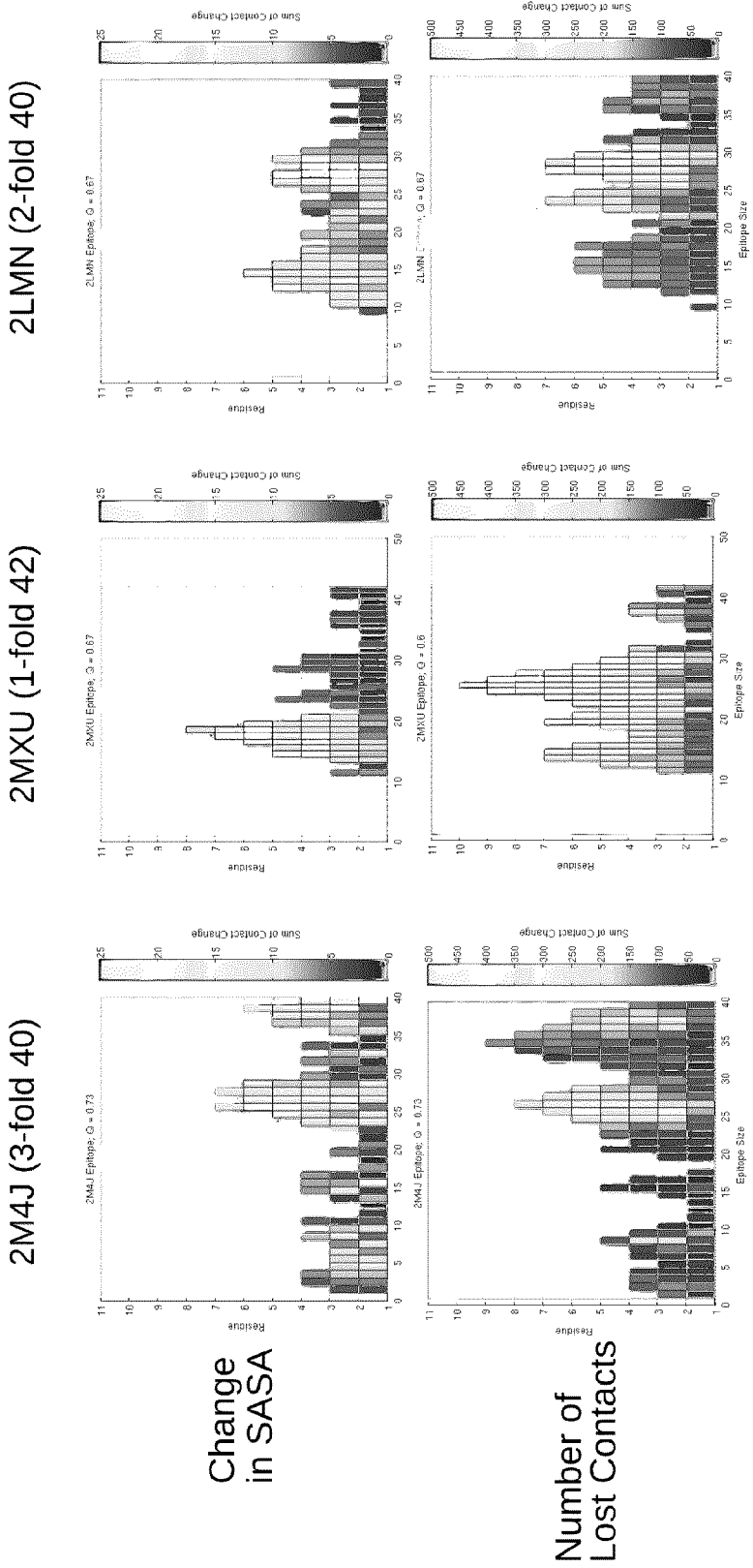
FIG. 9 shows a comparison of fireplots based on change in SASA (top row) and number of lost contacts (bottom row) for three different Aβ fibril structures (corresponding to the FIG. 9 columns).

In addition to or in the alternative to using SASA as a measure of disorder or exposure (local unfolding indicia 54), some embodiments may comprise considering the loss of contacts (from among the contacts in the native structure 22) as a local unfolding indicia 54. In this approach, the biasing simulations may be the same but the block 50 analysis may be slightly different. Instead of evaluating candidate epitopes by requiring that an epitope show increased ΔSASAn each residue for at least one chain in each simulation, such embodiments may comprise evaluating candidate epitopes by requiring that an epitope show a decrease in contacts (from among the contacts in the native structure 22) for each residue for at least one chain in each simulation. In practice, some embodiments may comprise setting a threshold, so that each residue not only has to decrease the number of contacts (from among the contacts in the native structure 22), but the change must be larger than some value—typically—0.5-1 contacts/atom. FIG. 9 shows a comparison of fireplots based on change in SASA (top row) and number of lost contacts (bottom row) for each of a number of proteins (corresponding to the FIG. 9 columns). Note that the biasing level for 2MXU is Q=0.67 in the top panel and Q=0.6 in the bottom panel. The longest epitopes predicted using Q are a length 9 epitope AEDVGSNKG (SEQ ID NO: 35) and 2 length 6 epitopes EVHHQK (SEQ ID NO: 36), VHHQKL (SEQ ID NO: 37). These overlap well with the epitopes in Table 1 for this particular strain, in particular: DVGSNKG (SEQ ID NO: 7), EDVGSN (SEQ ID NO: 19), QKLVF (SEQ ID NO: 20), HHQK (SEQ ID NO: 3), and AEDV (SEQ ID NO: 5).

Figure 14:
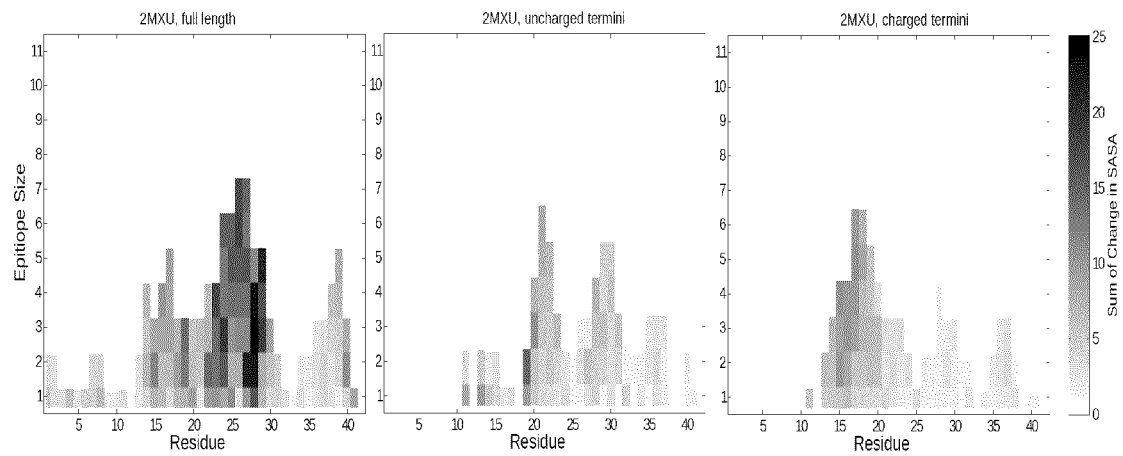
FIG. 14 shows fireplots for a number of different refinements to the method.

The inventor has examined the potential effects of selecting subsets of the full number of residues, and not adding an N-terminal region. In some embodiments, the simulation parameters by default assign one proton unit of positive charge to the N-terminal residue, however charge-charge repulsion might enhance disorder in the N-terminal region. FIG. 14 compares the different refinements to the method and the importance of each effect. In particular, the FIG. 14 plots show fireplots starting from the PDB structure without modification (right panel), for the structure with uncharged N-termini ($NH_2$ instead of $NH_3^+$, middle panel), and for the structure with the N-terminal residues 1-10 added back in (left panel). As described above, the default treatment of the N-terminus in many molecular dynamics simulations is a $NH_3^+$ group, which has a positive charge. Such a positive charge would result in an extra repulsion between the N-termini of the chains; in the real system the terminus is located elsewhere, roughly 10 residues earlier.

Figure 10:
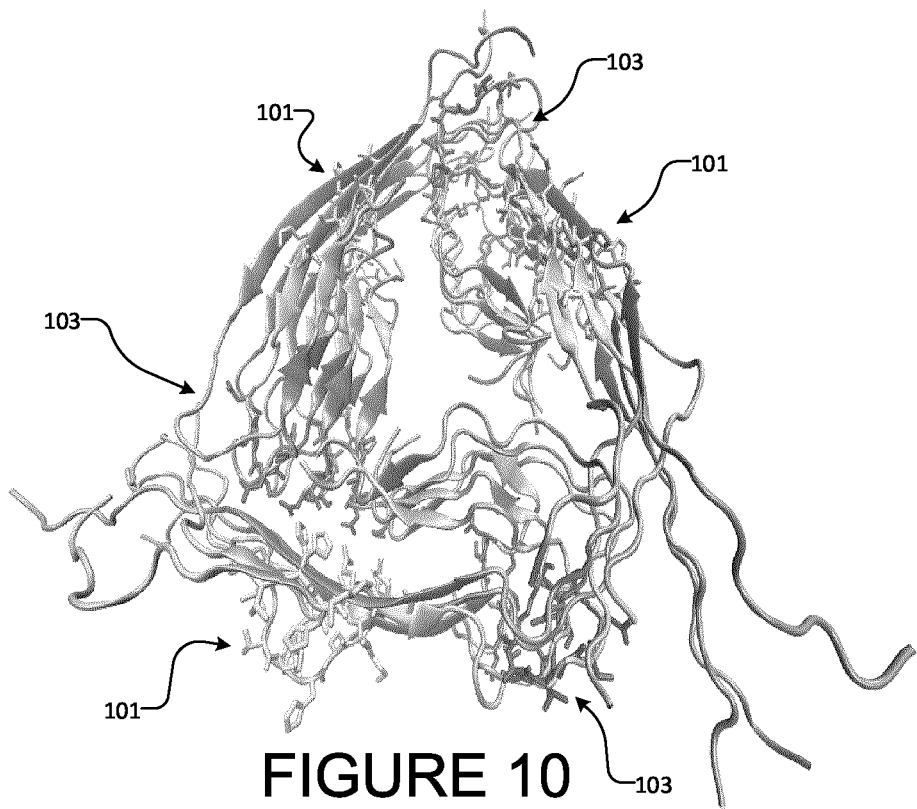
FIG. 10 is a rendering of the three-fold symmetric Aβ structure 2M4J after biasing to 0.8 of the initial Q.
Figure 11:
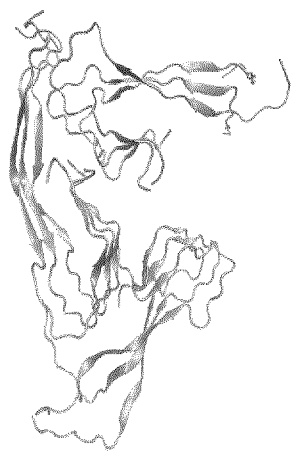
FIG. 11 is a rendering of the three-fold symmetric Aβ structure 2M4J after biasing to 0.6 of the initial Q.

FIG. 10 is a rendering of the three-fold symmetric Aβ structure 2M4J after biasing to 0.8 of the initial Q. The regions highlighted (by arrows 101, 103) are those predicted in FIG. 4A: residues 13 to 19 in light shade licorice rendering for the side chains (arrows 101) and residues 25 to 29 in darker shade licorice rendering for the side chains (arrows 103), in chain B. At stronger biasing (lower final Q), the fibril monomers begin to separate and open up (see FIG. 11). The FIG. 10 chains predicted to have residues 12-17 preferentially exposed upon biasing are all in the end layer of the three layers in the 2M4J structure Residues 25 to 29 in structure 2M4J form a turn between the two β sheets in the original structure. This region becomes exposed by breaking contacts with the N-terminal regions of the adjacent chains (FIG. 10). The final target collective coordinate bias value may be reduced sufficiently to disrupt the fibril. FIG. 7 has illustrated the robustness of the predictions with respect to the final target collective biasing coordinate. FIG. 11 shows that biasing the three-fold structure to 0.6 of initial Q rather than 0.8 distorts the protein significantly and increases the relative exposure of the turn in residues 25-29, which lose all contacts with the C-terminus of the adjacent chains. This does not change the epitope prediction, however, as this was an epitope predicted at the lower biasing level as well.

Figure 12:
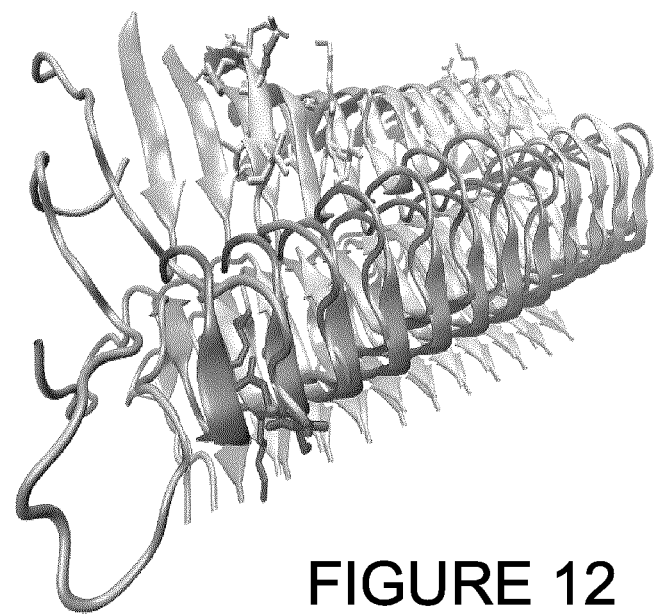

The Aβ42 structure 2MXU is a fibril that is 12 monomers long, which allows for an examination of the differences between end monomers and those in the middle. The residues 1 to 10 missing from the PDB structure have been reconstructed and added. The inventor has found that the end monomers of the 2MXU structure are much more prone to disorder those in the middle, which can be seen in FIG. 12. FIG. 12 is a rendering of the Aβ42 structure 2MXU after biasing to 0.8 of initial Q, which shows the end monomers detaching from the fibril. This shows the process of end-cap disorder/fragmentation. Since real fibrils may be composed of many more monomers than in this system, this issue has been addressed in some embodiments by restraining the chains on the ends (chains A and L), and repeating the biasing simulation.

Figure 13:
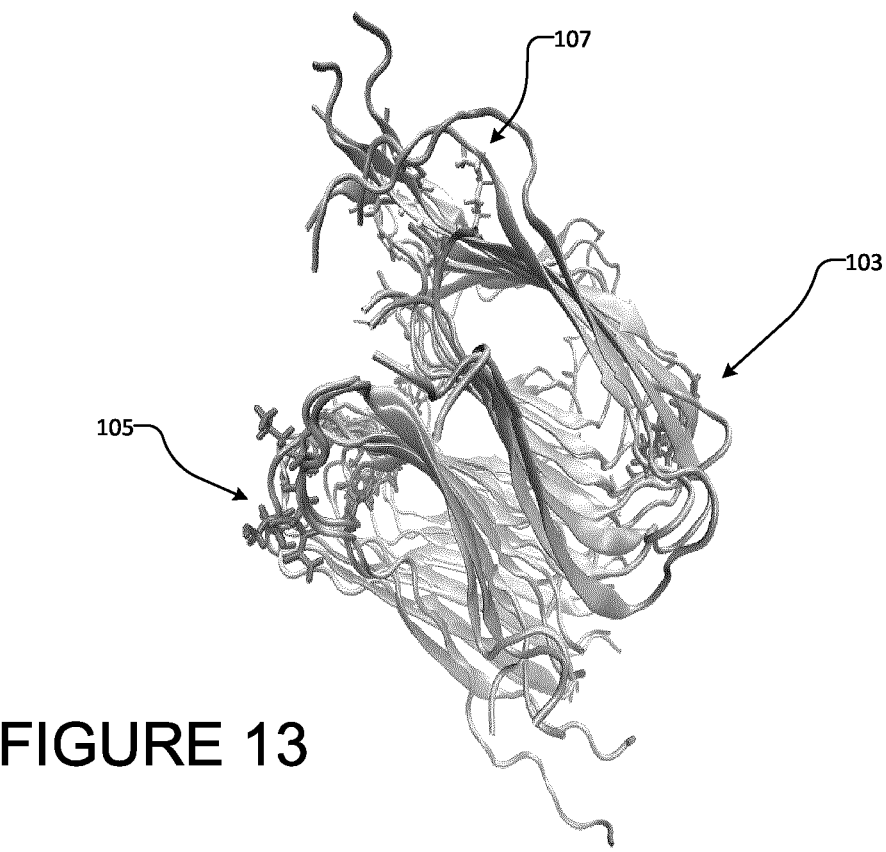
FIG. 13 shows a rendering of the 2-fold symmetric Aβ40 structure 2LMN after biasing to about 0.8 of initial Q.

A snapshot of the disordered structure superimposed on the initial structure for PDB 2LMN is shown in FIG. 13. For this two-fold symmetric structure, we again see residues 11-16 and 25-28, using licorice rendering for the side chains, emerging as predicted epitopes. FIG. 13 shows a rendering of the 2-fold symmetric Aβ40 structure 2LMN after biasing to about 0.8 of initial Q. The disordered configuration is superimposed on the initial configuration. The regions with sidechains highlighted correspond to chains J and K, residues 11 to 16 (dark shade, 105), and chains B, D, F, I residues 25-28 (light shade, 107).

Figure 17A:
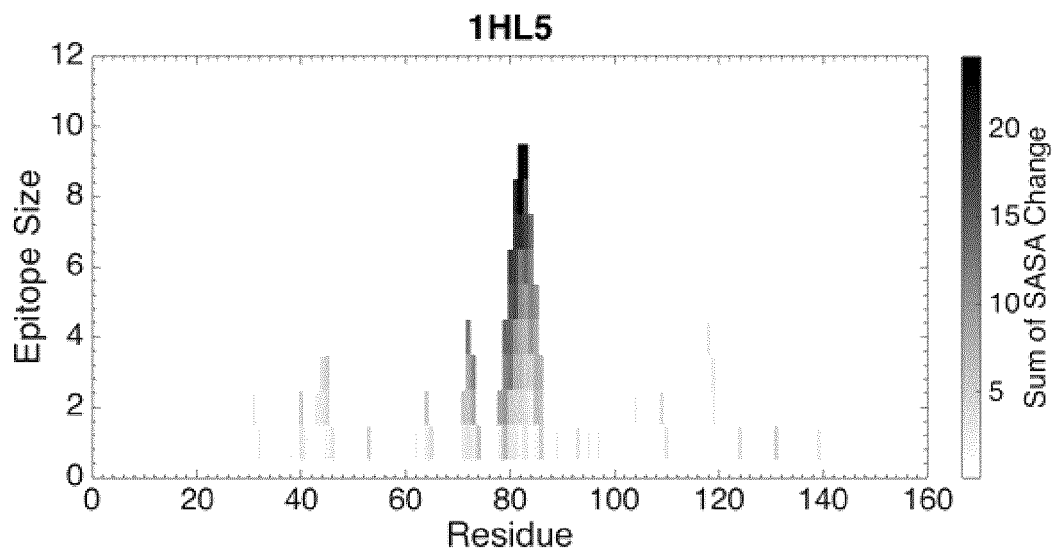
FIG. 17A is a fireplot for SOD1 which illustrates the analysis of potential candidate epitopes and prediction of candidate epitopes based on the output of the biasing process applied in the method of FIG. 1 according to a particular embodiment.
Figure 17B:
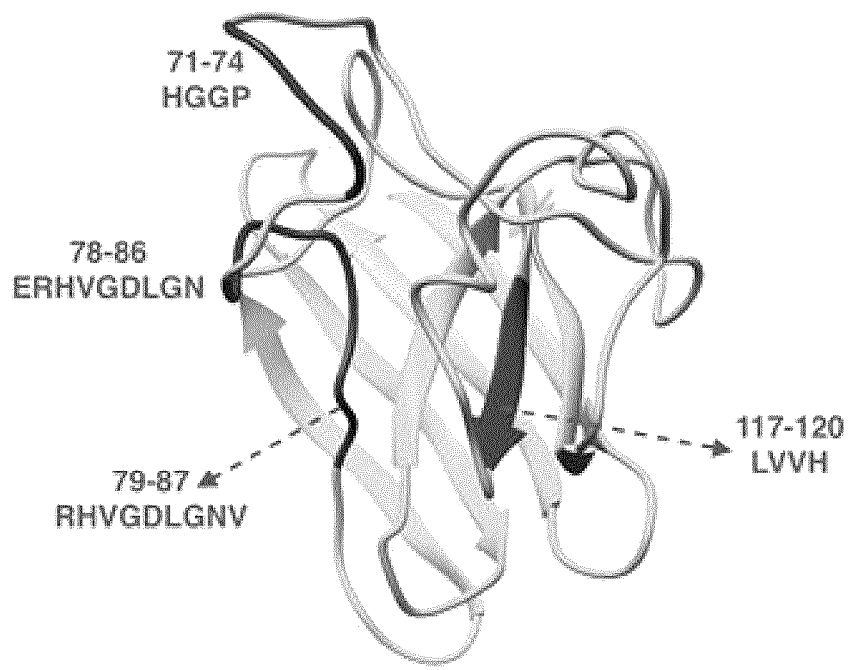
FIG. 17B is a illustrative representation of the biased ensemble of the FIG. 17A SOD1 at Q=0.65. Candidate epitopes are shown in darker shading.

The methods described herein may be applied to single-chain proteins. In one example experiment, the methods described herein were applied to a system constituting superoxide dismutase 1 (SOD1) lacking metals, but containing a disulfide bond between cysteines 57 and 146. The protein was biased on the global coordinate corresponding to the number of total contacts, and the target collective coordinate was reduced to a value of $Q_c=0.65$. The protein was then held at $Q_c=0.65$ and subsequently equilibrated for 90 ns. Snapshots were recorded every 20 ps, and the ΔSASA for each residue was measured in this ensemble of 4500 configurations. The procedure described in FIG. 5 (methods 102, 202) for constructing a data structure underlying a fireplot was followed to give FIG. 17A. The corresponding epitopes predicted from the fireplot data structure, following the procedure in FIG. 5C (method 302), are given in Table 3. These epitopes are shown in darker shading in FIG. 17B superimposed on a snapshot from the ensemble biased to $Q_c=0.65$.

TABLE 3

| PROTEIN | PDB ID | PREDICTED EPITOPE RESIDUES | EPITOPE SEQUENCE |
| --- | --- | --- | --- |
| SOD1, no metals, disulfide bond present | 1HL5 | 78-86 | ERHVGDLGN (SEQ ID NO: 38) |
| | | 79-87 | RHVGDLGNV (SEQ ID NO: 39) |
| | | 71-74 | HGGP (SEQ ID NO: 40) |
| | | 117-120 | LVVH (SEQ ID NO: 41) |

Table 3: Candidate epitopes for implementation of methods described herein on SOD1.

Figure 15:
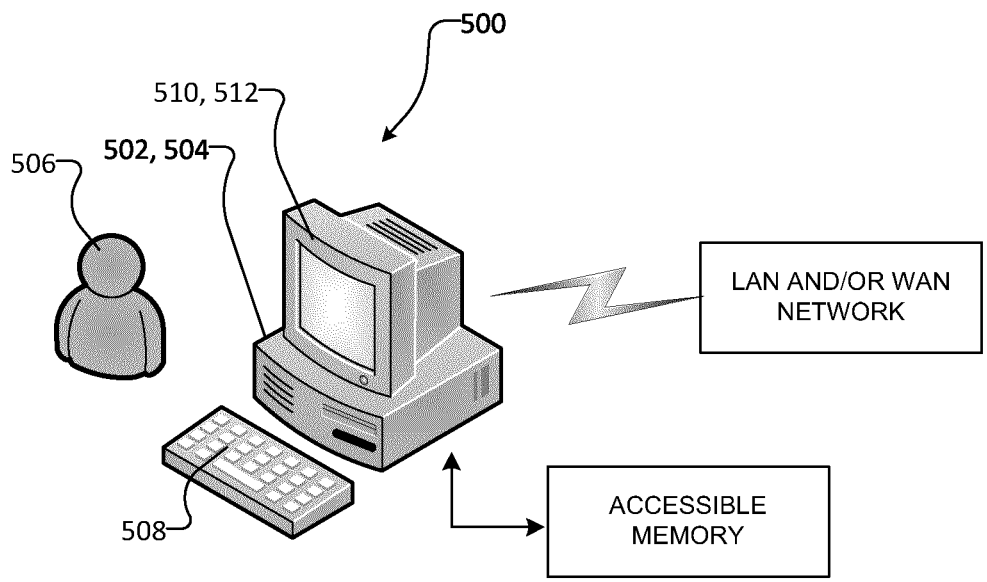
FIG. 15 is a schematic depiction of a computer system which may be used to perform any of the methods described herein and the steps of any of the methods described herein according to a particular embodiment.

FIG. 15 is a schematic depiction of a system 500 which may be used to perform any of the methods described herein and the steps of any of the methods described herein according to a particular embodiment. System 500 of the illustrated embodiment comprises one or more computers 502 which may comprise one or more processors 504 which may in turn execute suitable software (not expressly enumerated) accessible to processor(s) 504. When such software is executed by computer 502 (and in particular processor(s) 504), computer 502 and/or processor(s) 504 may perform any of the methods described herein and the steps of any of the methods described herein. In the illustrated embodiment, computer 502 provides an optional user interface 510 for interaction with a user 506. From a hardware perspective, user interface 510 comprises one or more input devices 508 by which user 506 can input information to computer 502 and one or more output devices 512 by which information can be output to user 506. In general, input devices 508 and output devices 512 are not limited to those shown in the illustrated embodiment of FIG. 15. In general, input device 508 and output device 512 may comprise any suitable input and/or output devices suitable for interacting with computer 502. User interface 510 may also be provided in part by software when such software is executed by computer 502 and/or its processor(s) 504. In the illustrated embodiment, computer 502 is also connected to access data (and/or to store data) on accessible memory device 518. In the illustrated embodiment, computer 502 is also connected by communication interface 514 to a LAN and/or WAN network 516, to enable accessing data from networked devices (not shown) and/or communication of data to networked devices.

Input may be obtained by computer 502 via any of its input mechanisms, including, without limitation, by any input device 508, from accessible memory 518, from network 516 or by any other suitable input mechanism. The outputs may be output from computer 502 via any of its output mechanisms, including, without limitation, by any output device 512, to accessible memory 518, to network 516 or to any other suitable output mechanism. As discussed above, FIG. 15 is merely a schematic depiction of a particular embodiment of a computer-based system 500 suitable for implementing the methods described herein. Suitable systems are not limited to the particular type shown in the schematic depiction of FIG. 15 and suitable components (e.g. input and output devices) are not limited to those shown in the schematic depiction of FIG. 15.

The methods described herein may be implemented by computers comprising one or more processors and/or by one or more suitable processors, which may, in some embodiments, comprise components of suitable computer systems. By way of non-limiting example, such processors could comprise part of a computer-based automated contract valuation system. In general, such processors may comprise any suitable processor, such as, for example, a suitably configured computer, microprocessor, microcontroller, digital signal processor, field-programmable gate array (FPGA), other type of programmable logic device, pluralities of the foregoing, combinations of the foregoing, and/or the like. Such a processor may have access to software which may be stored in computer-readable memory accessible to the processor and/or in computer-readable memory that is integral to the processor. The processor may be configured to read and execute such software instructions and, when executed by the processor, such software may cause the processor to implement some of the functionalities described herein.

Certain implementations of the invention comprise computer processors which execute software instructions which cause the processors to implement a controller and/or perform a method of the invention. For example, one or more processors in a computer system may implement data processing steps in the controllers and/or methods described herein by executing software instructions retrieved from a program memory accessible to the processors. The invention may also be provided in the form of a program product. The program product may comprise any medium which carries a set of computer-readable signals comprising instructions which, when executed by a data processor, cause the data processor to implement a controller and/or execute a method of the invention. Program products according to the invention may be in any of a wide variety of forms. The program product may comprise, for example, physical (non-transitory) media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, controller, processor, assembly, device, component, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Interpretation of Terms

Unless the context clearly requires otherwise, throughout the description and the

- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof; elements which are integrally formed may be considered to be connected or coupled;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

in different directions, and/or be offset from each other by a space and/or an angle.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs")). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a computer system for a device may implement methods as described herein by executing software instructions in a program memory accessible to the processors.

Processing may be centralized or distributed. Where processing is distributed, information including software and/or data may be kept centrally or distributed. Such information may be exchanged between different functional units by way of a communications network, such as a Local Area Network (LAN), Wide Area Network (WAN), or the Internet, wired or wireless data links, electromagnetic signals, or other data communication channel.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Embodiments of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in software. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Where a record, field, entry, and/or other element of a database is referred to above, unless otherwise indicated, such reference should be interpreted as including a plurality of records, fields, entries, and/or other elements, as appropriate. Such reference should also be interpreted as including a portion of one or more records, fields, entries, and/or other elements, as appropriate. For example, a plurality of "physical" records in a database (i.e. records encoded in the database's structure) may be regarded as one "logical" record for the purpose of the description above and the claims below, even if the plurality of physical records includes information which is excluded from the logical record.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

While a number of exemplary aspects and embodiments have been discussed above, those of skill in the art will recognize certain modifications, permutations, additions and subcombinations thereof. For example:

In some embodiments, the protein under consideration may be biased to lose native structure by using solvent-accessible surface area (SASA), rather than using native contacts.

In some embodiments, analyzing the results of the biasing (e.g. block 50) may comprise measuring the regions having the most significant increase in dynamics once biased, in addition to or in the alternative to an increase in surface area (SASA) or a loss of initial contacts, may also indicate which regions are structurally disrupted and more prone to partake in non-native interactions. An example of such a measure of increased dynamics may comprise the root mean squared fluctuations (RMSF) of an amino acid.

Some embodiments may comprise direct computational measurement of the loss of potential energy of a particular amino acid sequence upon biasing may serve as a proxy for structural change upon biasing.

Some embodiments may comprise the measurement of backbone hydrogen bonds lost from among the backbone hydrogen bonds of the native structure, which may serve as a collective coordinate for biasing or a subsequent indicia of local unfolding (e.g. local loss of native structure).

The embodiments described above make use of a molecular dynamics engine to simulate changes in protein structure upon the application of bias. In some embodiments, a Monte Carlo dynamics engine may be used in addition to or in the alternative to a molecular dynamics engine. Either or both of a molecular dynamics engine and a Monte Carlo dynamics engine may be referred to herein as a conformational sampling engine for proteins or aggregated fibril structures.

In some embodiments, the protein under consideration may be biased to lose native structure by using metadynamics in addition to or in the alternative to applying a bias potential based on an order parameter such as SASA relative to the native SASA or the number of contacts from among the native contacts.

Pseudocode illustrating details of steps and methods of particular non-limiting example embodiments is described below:

Pseudocode Corresponding to Methods 102, 202 (FIGS. 5A and 5B)

% Determine/Record ΔSASA

```
For each run, where 1< run< Nruns % Nruns is typically set to 10
    For each chain , where 1< chain < Nchains % Number of chains in the simulated
fibril
        for each res , where 1<r<Nres
            Calculate <ΔSASA> (res, run,chain) % for each residue res in each
            chain, in each run, ΔSASA is the change in solvent accessible surface
            area, and <..> indicates the equilibrium average over snapshots of
            configurations for the system. A snapshot every 20ps for a typical
            100ns simulation gives 100ns/20ps = 5000 snapshots. This quantity is
            hereafter understood to be equilibrium averaged, so that <ΔSASA> =
            ΔSASA.
        end for res
    end for chain
    Write ΔSASA into a separate data file for each run; % format is two columns: 1$^{st}$
    column = res , 2$^{nd}$ column is ΔSASA. Location of chain j , residue k in the file is
    given by row Nres*j+k. % each file contains multiple chains
end for run % End Determine/Record ΔSASA
```

% After all data files from all runs are read in for input, ΔSASA is a 3D rectangular matrix of size (Nrun×Nchain× Nres)

% Define a new matrix DSASAwindowed, for the fireplots which consists of ΔSASA values for each window position wp, window size ws.

DSASAwindowed(wp,ws)=0 all wp, ws % where wp is window position 1<wp<Nres (in the for loop values are assigned for a subset of these positions), ws is window size 1<ws<wsmax defined below.

% size of DSASAwindowed is Nres×wsmax; loops below don't run from 1:Nres; elements outside the for loop below are never changed from zero.

% Guess a max window size wsmax; typically about 12 amino acids/residues. The max window size will have 0 "hits" in it. I.e. zero successes as defined below. This only means we are ending with a window size that is above the peaks in the fireplots that are produced.

Set fmin=the minimum fraction for success. % This is taken to allow some runs by chance to stochastically not exhibit localized unfolding. Since we typically implement Nruns=10 runs, we have taken this to be 0.9, meaning at least 9 out of 10 runs must result in a localized unfolding "hit", a localized unfolding "hit" being increased SASA exposure for all residues in the window.

% Build "fireplot" data structure
% Input to the loop below is ΔSASA (res,run,chain), an array of size (Nres×Nrun×Nchain)

for window size ws=1:wsmax % i.e. increment until the window size is wsmax; wsmax can either be the total chain length Nres, or can be a window size that is expected to be larger than any of the contiguous strands that show an increase in surface area; in practice wsmax might be set to 12)

% implement the Build_fireplot function defined below, window center position=wp DSASAwindowed(:,ws)=Buildfireplot function(ΔSASA(res,run,chain), ws, fmin); % the Build_fireplot functions returns a vector of length Nres, fill the 2D array with this vector end for window size write DSASAwindowed(wp,ws) to file % array of Nres× wsmax written to file for each protein or fibril model % Output from the above loop is DSASAwindowed(wp,ws), an array of size Nres×wsmax, for the native protein or fibril model.

% Build_fireplot function call in the above pseudocode:
begin Build_fireplot function % function (ΔSASA(res,run, chain), ws, fmin) in the above loop is defined as follows:

```
DSASAwindowed(:, ws) = 0; % initialize the output DSASAwindowed to a vector of Nres
zeros
count(:,:) = 0; % this is a Boolean matrix of 1's and 0's of size Nres × Nrun, used only
within Build_fireplot function to check the fmin criterion
    for run = 1:Nruns % in the example of Figure 4B Nruns=3, and Nchains=3
        for window centre position wp = wpmin: wpmax % (here wpmin = round(
        ws/2) is the initial window position for a given window size ws. E.g. if ws is 7,
        then wpmin is 4, defined as the integer just after 3.5, whereas if ws=6 ,
        wpmin=3; wpmax = Nres – (ws –wpmin) )
        for chain=1:Nchains
            if (for all res in window defined by (wp,ws),
        ΔSASA(res,run,chain) > 0) ,
                % in Fig 4B, this if statement is true for (Run,Chain) = (1,2),
                (2,1), (3,2), and (3,3)
                then
                    DSASAwindowed(wp,ws) = sum on res in window of
                    size ws of ΔSASA(res,run,chain);
```

-continued

```
            count(wp,run) = 1;
          end if ΔSASA > 0
       end for chain
    end for wp % have now checked all chains at all positions in one given run
            for any hits
end for runs % DSASAwindowed(wp,ws) has now been summed over chains, and
over runs; I.e. in Fig 4B, the SASA from four panels, (run,chain)= (1,2), (2,1), (3,2),
and (3,3) have all been summed. In Fig 4B, there was a hit in every run at least for
one chain, so count(wp,run) at that window position illustrated is a vector of [1 1 1].
```

% check whether number of runs satisfies the fmin fraction requirement (count=1 appears in 9/10 runs), if not set the corresponding DSASA(wp,ws0)=0:
starting_element=floor((1−fmin)*Nruns)+1; % the array starting element, that sets the number of runs for which the epitope must appear. For fmin=0.9 and Nruns=10, starting_element=2 here, and the epitope must appear in elements 2 through 10. for wp=1:Nres
countsort=sort(count(wp,:)) % count(wp,:) is a vector of length Nruns of 1's and 0's, e.g. [1 1 0 0 1 1 0 1 1 1]; sort(count(wp,:)) turns this into [0 0 0 1 1 1 1 1 1 1]; 0 indicates no epitope prediction (i.e., not all residues in the segment (wp,ws) increased SASA), 1 indicates that the epitope is predicted (i.e., all residues in the segment (wp,ws) have increased SASA).
if (any(countsort(starting_elementend)==0)) % (skip the first (starting_element-1) runs status (meaning we allow starting_element-1 runs to miss the prediction); For the remaining elements of the countsort matrix (i.e. countsort(ss:end)), if any element is 0 (meaning there are more than ss-1 runs missing the prediction), then we will set the corresponding DSASAwindowed(wp,ws)=0:
DSASAwindowed (wp, ws)=0; % zero elements in DSASAwindowed mean that the matrix does not predict an epitope in that location. Even if at this point there was a non-zero sum of SASA in this matrix, if it fails the run threshold criterion, its value is reset to zero.
end if
end for wp return DSASAwindowed(wp,ws); returns DSASAwindowed(:,ws0)
end Build_fireplot function Pseudocode Corresponding to Method 302 (FIG. 5C)

% Use Fireplot data structure to predict candidate epitopes
% Input (from above) would be DSASAwindowedTotal(wp, ws). i.e. the data in the fireplots.

for ws=wmax−1:3% decrease the window size from it's maximum value (e.g. wsmax=11 in FIG. 6A) down to a minimum of 3. We consider epitopes of length 3 and larger here. This is arbitrary and could have been reduced to 4. The shorter the epitope length, the more commonly it will appear in the proteome, and the more likely it is to suffer from off-pathway targets. Taking a length of 3 allows the epitope to be short enough to provide a well-defined target within the protein, but long enough to be relatively unique within the proteome in terms of the sequence identity and the conformation.

```
for wp = 1:Nres
    if (wp is a hit) % i.e. if there is a value of DSASAwindowedTotal(wp,ws)>0
         for the window position wp.
            record the epitope(wp,ws) % For example, in Fig 6A the 1ˢᵗ hit
            would correspond to (wp=26 ws=7) or an epitope of length 7 centered
            at position 26: [23 24 25 26 27 28 29]; residues 23-29 is thus the
            longest epitope for 2M4J in Table 1, and is rendered as the longest
            horizontal box in Figure 8 for 2M4J, corresponding to DVGSNKG
            (SEQ ID NO: 7).
            remove all the sub-epitopes that lie within the epitope in question
            % in the fireplot of Fig 6A, this would correspond to removing
            rectangles in the following coordinates: remove (26,7)
            % then (25,6) and (26,6) (these make sub-epitopes that are all within
            the length 7 epitope, i.e. 23-28 and 24-29)
            % then (25,5) (26,5) (27,5) (these also make sub-epitopes that are all
            within the length 7 epitope)
            % then (24,4) (25,4) (26,4) (27,4)
            % then (24,3) (25,3) (26,3) (27,3) (28,3)
            % then (23,2) (24,2) (25,2) (26,2) (27,2) (28,2)
            % then finally (23,1) (24,1) (25,1) (26,1) (27,1) (28,1) (29,1)
            % The plot with the corresponding "ablated cone" is in Figure 16 in
            the transition from (A) → (B). More epitopes, possibly overlapping
            ones, are found as we continue the ablation process down to epitopes of
            length 4.
    end if wp is a hit
    end for wp
end for ws
```

% For FIG. 6A, 2M4J, after 1ˢᵗ ablation—the next largest epitope we are left with is (27,6), or epitope [25 26 27 28 29 30] (residues 25-30 in Table 1, which overlaps with the 1ˢᵗ epitope) % You can see the corresponding cone being ablated in the transition from FIG. 16 (B)→(C)
% we repeat the ablation process until and including epitope lengths of 3.
% what results is a set of epitope predictions, of length 3 and higher.
% These epitopes are given in Table 1 and FIG. 8.

What is claimed is:

1. A method for computer-based prediction of one or more candidate epitopes in a protein, the method comprising:
providing, on a computer system, a conformational sampling engine;
obtaining, at the computer system, a model of a protein suitable for use with the conformational sampling engine, the obtained protein model comprising a native structure;
applying, by the computer system, a collective coordinate bias to the protein model, the applying comprising instructing the conformational sampling engine to force the protein model to at least partially unfold from its native structure to an updated structure, wherein the collective coordinate bias is applied globally to at least a substantial portion of the protein model and is impartial as to where, within the substantial portion of the protein model, unfolding occurs, and wherein applying the collective coordinate bias to the protein model comprises increasing, decreasing or otherwise varying or manipulating an externally applied target collective coordinate to apply a corresponding biasing potential to the protein model and performing, by the computer system, a discrete time simulation on the protein model over a plurality of time steps, the discrete time simulation starting with the native structure for the protein model and, in each particular time step from among the plurality of time steps, generating a corresponding updated structure for the protein model for the particular time step;
analyzing, by the computer system, the updated structure resulting from the application of the collective coordinate bias to detect indicia of localized unfolding and identify one or more candidate epitopes, wherein a candidate epitope is a group of residues that exhibits one or more indicia of localized unfolding;
the analyzing comprising creating and displaying by the computer system a data file containing a data structure indexed by residue, and a value for a local unfolding indicator, wherein each entry in the matrix data structure comprises a potential candidate epitope and selecting one or more candidate epitopes associated with the updated structure; and
making an immunogen comprising the one or more selected candidate epitope sequences.

2. A method according to claim 1, wherein obtaining the model of the protein comprises obtaining the protein model from a database of protein models or obtaining a first structure for the protein model and then modifying, by the computer system, the first structure for the protein model to generate the native structure for the protein model; optionally wherein
A) modifying the first structure for the protein model to generate the native structure for the protein model comprises performing, by the computer system, an equilibration simulation on the protein model, wherein performing the equilibration simulation on the protein model comprises subjecting the protein model with the first structure to a model environment characterized by one or more of: a constant number of particles, a constant pressure and a constant temperature; or
B) wherein modifying the first structure for the protein model to generate the native structure for the protein model comprises adding one or more missing residues to the first structure to generate the native structure, the native structure corresponding to a full length primary sequence.

3. A method according to claim 1, wherein performing the discrete time simulation on the protein model over the plurality of time steps comprises causing the conformational sampling engine to force structural changes in the protein model, which structural changes are determined by requiring an actual collective coordinate determined from the updated structure for the protein model to track the target collective coordinate over the plurality of time steps and wherein requiring an actual collective coordinate determined from the updated structure for the protein to track the target collective coordinate over the plurality of time steps comprises:
A) requiring, at each particular time step from among the plurality of time steps, the actual collective coordinate determined from the updated structure for the protein at the particular time step to track the target collective coordinate for the particular time step;
B) minimizing, by the computer system, free energy of the protein model subject to a potential energy function, the potential energy function depending, at least in part, on a metric which expresses a difference between the actual collective coordinate for any arbitrary structure of the protein model and the target collective coordinate; or
C) minimizing, by the computer system, a potential energy function, the potential energy function depending, at least in part, on a metric which expresses a difference between the actual collective coordinate for any arbitrary structure of the protein model and the target collective coordinate, preferably wherein minimizing the potential energy function comprises minimizing the potential energy function at each particular time step from among the plurality of time steps.

4. A method according to claim 3, wherein the potential energy function comprises a term of the form:

$$V(Q,t)=\tfrac{1}{2}k(Q-Q_c(t))^2$$

where $Q_c(t)$ is the target collective coordinate and $Q$ is the actual collective coordinate for any arbitrary structure of the protein model and $k$ is a configurable constant.

5. A method according to claim 3, wherein, over the plurality of time steps of the discrete time simulation, the target collective coordinate starts at an initial target collective coordinate value equal to that of the actual collective coordinate associated with the native structure, changes over a first sub-plurality of time steps to a final target collective coordinate value and then stays at the final target collective coordinate value for a second plurality of time steps; optionally wherein over the plurality of time steps of the discrete time simulation, i) the target collective coordinate changes smoothly over time; or ii) the target collective coordinate changes at a constant rate over time between the initial target collective coordinate value and the final target collective coordinate value.

6. A method according to claim 3,
A) wherein the actual collective coordinate determined for any updated structure for the protein model is based at least in part on a number of contacts between heavy atoms in the updated structure of the substantial portion of the protein model from among the contacts between heavy atoms in the native structure of the substantial portion of the protein model;
B) wherein the actual collective coordinate determined for any updated structure for the protein model is based at least in part on a contact function which approximates number of contacts between heavy atoms in the updated structure of the substantial portion of the protein model from among the contacts between heavy atoms in the native structure of the substantial portion of the protein model;

C) wherein for each contact from among the contacts in the native structure of the substantial portion of the protein model, the contact function has the form:

$$Q_{ij} = \frac{1 - \left(\frac{r_{ij}}{r_0}\right)^n}{1 - \left(\frac{r_{ij}}{r_0}\right)^m}$$

where $r_{ij}$ is the distance between the nuclei of atoms i and j in the substantial portion of the protein model and $r_0$, n and m are suitably selected constants;

D) wherein the actual collective coordinate determined for any updated structure for the protein model is based at least in part on distances between heavy atoms in the updated structure of the substantial portion of the protein model relative to distances between heavy atoms in the native structure of the substantial portion of the protein model;

E) wherein the actual collective coordinate determined for any updated structure for the protein model is based at least in part on a root-mean square structural deviation (RMSD) in the updated structure of the substantial portion of the protein model relative to the RMSD of the native structure of the substantial portion of the protein model, the RMSD defined through positions of at least one of: alpha carbon atoms of the substantial portion of the protein model and heavy atoms of the substantial portion of the protein model;

F) wherein the actual collective coordinate determined for any updated structure for the protein model is based at least in part on a total solvent accessible surface area (SASA) of the updated structure of the substantial portion of the protein model relative to the SASA of the native structure of the substantial portion of the protein model;

G) wherein the actual collective coordinate determined for any updated structure for the protein model is based at least in part on a number of backbone hydrogen bonds in the updated structure of the substantial portion of the protein model from among the backbone hydrogen bonds in the native structure of the substantial portion of the protein model;

H) wherein the actual collective coordinate determined for any updated structure for the protein model is based at least in part on a radius of gyration of the updated structure of the substantial portion of the protein model relative to the radius of gyration of the native structure of the substantial portion of the protein model;

I) wherein the actual collective coordinate determined for any updated structure for the protein model is based at least in part on a structural overlap function of the updated structure of the substantial portion of the protein model relative to the structural overlap function of the native structure of the substantial portion of the protein model; or J) wherein the actual collective coordinate determined for any updated structure for the protein model is based at least in part on a generalized Euclidean distance of the updated structure of the substantial portion of the protein model from the native structure of the substantial portion of the protein model.

7. A method according to claim 1 comprising repeating the step of applying the collective coordinate bias to the protein model in one or more independent runs; optionally comprising, for each run, determining, by the computer system and for each residue from among a plurality of residues in the updated structure for the protein model, the local unfolding indicator which provides a metric indicative of unfolding of the protein at the residue, optionally further comprising creating, by the computer system, a matrix data structure indexed by run and by residue, the matrix data structure comprising, for each run and each residue from among the plurality of residues, a value for the corresponding local unfolding indicator.

8. A method according to claim 7 comprising, for each run and each residue from among the plurality of residues, determining the local unfolding indicator based on an average over a plurality of updated structures for the protein model; optionally wherein, for each run and each residue from among the plurality of residues, the applied collective coordinate bias is constant for the plurality of updated structures over which the average is determined.

9. A method according to claim 7,
A) wherein, for each run and each residue from among the plurality of residues in the updated structure for the protein model, the local unfolding indicator is based at least in part on a change in solvent-accessible surface area (SASA) for the residue in the updated structure for the protein model relative to the SASA for the residue in the native structure for the protein model;
B) wherein, for each run and each residue from among the plurality of residues in the updated structure for the protein model, the local unfolding indicator is based at least in part on a number of lost contacts between atoms for the residue in the updated structure model for the protein model from among a plurality of contacts between atoms for the residue in the native structure for the protein model;
C) wherein, for each run and each residue from among the plurality of residues in the updated structure for the protein model, the local unfolding indicator is based at least in part on a root mean squared fluctuations (RMSF) of the residue for updated structure model for the protein model relative to the RMSF of the residue for the native structure for the protein model;
D) wherein, for each run and each residue from among the plurality of residues in the updated structure for the protein model, the local unfolding indicator is based at least in part on a number of lost backbone hydrogen bonds in the residue of the updated structure model for the protein model from among a plurality of hydrogen bonds in the residue of the native structure for the protein model; and/or
E) wherein, for each run and each residue from among the plurality of residues in the updated structure for the protein model, the local unfolding indicator is based at least in part on a potential energy of interaction for the residue in the updated structure model for the protein model relative to the potential energy of interaction for the residue in the native structure for the protein model.

10. A method according to claim 7, wherein, for each run, analyzing the updated structure to identify the one or more candidate epitopes comprises parsing, by the computer system, the updated structure for the protein model into a plurality of groups of residues and, for each group, subjecting, by the computer system, the local unfolding indicia for the group to a group unfolding assessment, the group unfolding assessment returning a positive unfolding assessment result for the group if all or more than a suitable threshold fraction of the residues in the group have local unfolding indicia indicative of unfolding; optionally wherein assessing whether any one local indicator is indicative of unfolding comprises subjecting, by the computer system, the one local indicator to a thresholding process.

11. A method according to claim 10,
A) wherein the plurality of groups comprise various window sizes, wherein the window size of a particular group refers to a number of residues in the particular group, optionally wherein some of the plurality of groups include common residues;
B) wherein the plurality of groups comprises a plurality of sets of groups, each set of groups having a common window size and each set of groups including all of the residues in the plurality of residues; or
C) wherein for each run and each residue from among the plurality of residues in the updated structure for the protein model, the local unfolding indicator is based at least in part on a change in solvent-accessible surface area (SASA) for the residue in the updated structure for the protein model relative to the SASA for the residue in the native structure for the protein model and wherein subjecting the local unfolding indicia for the group to a group unfolding assessment comprising returning a positive results for the group if all or more than a suitable threshold fraction of the residues in the group have a change in SASA that is greater than zero (ASASA>0).

12. A method according to claim 10 comprising, for each of the plurality of groups of residues, considering, by the computer system, the group of residues to be a potential candidate epitope based on determining, by the computer system, the group of residues to exhibit a positive unfolding assessment result over a number of runs greater than or equal to a threshold fraction (f) of a total number of runs; preferably
A) comprising accumulating, for each potential candidate epitope, the local unfolding indicia for the residues in the group of residues corresponding to the potential candidate epitopes; wherein the accumulated local unfolding indicia for each potential candidate epitope are indicative of a strength of the potential candidate epitope;
B) comprising creating, by the computer system, a matrix data structure indexed by window size and a group residue reference wherein each entry in the matrix data structure comprises a potential candidate epitope, the residues that make up the potential candidate epitope and optionally the accumulated local unfolding indicia for the residues that make up the potential candidate epitope; and/or
C) comprising identifying a first candidate epitope from among the potential candidate epitopes, wherein identifying the first candidate epitope comprises selecting the potential candidate epitope having the largest window size to be the first candidate epitope; optionally after identifying the first candidate epitope, removing the first candidate epitope and sub-epitopes of the first candidate epitope from among the potential candidate epitopes to obtain a reduced set of potential candidate epitopes for further consideration as candidate epitopes, the sub-epitopes of the first epitope comprising groups of epitopes that are smaller than the first candidate epitope and that include only residues also contained in the first candidate epitope; optionally comprising repeating the steps of:
identifying a next candidate epitope from among the reduced set of potential candidate epitopes, wherein identifying the next candidate epitope comprises selecting the potential candidate epitope having the largest window size in the reduced set of potential candidate epitopes to be the next candidate epitope; and
removing the next candidate epitope and sub-epitopes of the next candidate epitope from among the reduced set of potential candidate epitopes, the sub-epitopes of the next epitope comprising groups of epitopes that are smaller than the next candidate epitope and that include only residues also contained in the next candidate epitope;
until the largest window size in the reduced set of potential candidate epitopes is less than or equal to a threshold minimum size.

13. A method according to claim 1,
A) wherein the protein is an aggregated structure and the native structure comprises a native structure exhibited by peptide chains of the aggregated structure;
B) wherein the protein is a single chain polypeptide with putative folded structure;
C) wherein the substantial portion of the protein model comprises all of the protein model;
D) wherein the substantial portion of the protein model comprises all of the protein model except for a boundary structure; and/or
E) wherein the protein is an aggregated structure and the substantial portion of the protein model comprises all of the protein model corresponding to the aggregated structure except for boundary peptide chains at ends of the aggregated structure.

14. A method according to claim 7, wherein the protein is an aggregated structure and the native structure comprises a native structure exhibited by peptide chains of the aggregated structure and wherein, for each run, analyzing the updated structure to identify the one or more candidate epitopes comprises parsing, by the computer system, the updated structure for the protein model into a plurality of groups of residues and, for each group, subjecting, by the computer system, the local unfolding indicia for the group to a group unfolding assessment, the group unfolding assessment returning a positive unfolding assessment result for the group if all or more than a suitable threshold fraction of the residues in the group have local unfolding indicia indicative of unfolding for any peptide chain in the aggregated structure.

15. The method of claim 4, wherein the potential energy function also depends on molecular dynamic forces inherent in or otherwise associated with the protein model and/or wherein minimizing the potential energy function comprises minimizing the potential energy function subject to constraints imposed on the basis of molecular dynamic forces inherent in or otherwise associated with the protein model.

16. The method of claim 3, wherein the actual collective coordinate determined for any updated structure for the protein model comprises a metric indicative of global unfolding of the updated structure of the substantial portion of the protein model relative to the native structure of the substantial portion of the protein model.

17. A method for making an immunogen, the method comprising:
providing, on a computer system, a conformational sampling engine;

obtaining, at the computer system, a model of a protein suitable for use with the conformational sampling engine, the obtained protein model comprising a native structure;

applying, by the computer system, a collective coordinate bias to the protein model, the applying comprising instructing the conformational sampling engine to force the protein model to at least partially unfold from its native structure to an updated structure, wherein the collective coordinate bias is applied globally to at least a substantial portion of the protein model and is impartial as to where, within the substantial portion of the protein model, unfolding occurs, and wherein applying the collective coordinate bias to the protein model comprises increasing, decreasing or otherwise varying or manipulating an externally applied target collective coordinate to apply a corresponding biasing potential to the protein model and performing, by the computer system, a discrete time simulation on the protein model over a plurality of time steps, the discrete time simulation starting with the native structure for the protein model and, in each particular time step from among the plurality of time steps, generating a corresponding updated structure for the protein model for the particular time step;

analyzing, by the computer system, the updated structure resulting from the application of the collective coordinate bias to detect indicia of localized unfolding and identify one or more candidate epitopes, wherein a candidate epitope is a group of residues that exhibits one or more indicia of localized unfolding;

the analyzing comprising creating by the computer system a data file containing a data structure indexed by residue, and a value for a local unfolding indicator, wherein each entry in the matrix data structure comprises a potential candidate epitope and identifying one or more candidate epitopes associated with the updated structure;

selecting a candidate epitope sequence from the one or more identified candidate epitopes associated with the updated structure, and making an immunogen comprising the selected candidate epitope sequence.

18. The method of claim 17, wherein obtaining the model of the protein comprises obtaining the protein model from a database of protein models or obtaining a first structure for the protein model and then modifying, by the computer system, the first structure for the protein model to generate the native structure for the protein model; optionally wherein A) modifying the first structure for the protein model to generate the native structure for the protein model comprises performing, by the computer system, an equilibration simulation on the protein model, wherein performing the equilibration simulation on the protein model comprises subjecting the protein model with the first structure to a model environment characterized by one or more of: a constant number of particles, a constant pressure and a constant temperature; or B) wherein modifying the first structure for the protein model to generate the native structure for the protein model comprises adding one or more missing residues to the first structure to generate the native structure, the native structure corresponding to a full length primary sequence.

* * * * *